United States Patent
Mao et al.

(10) Patent No.: US 8,828,204 B2
(45) Date of Patent: *Sep. 9, 2014

(54) REDOX POLYMERS

(75) Inventors: Fei Mao, Fremont, CA (US); Adam Heller, Austin, TX (US)

(73) Assignee: Abbott Diabetes Care Inc., Alameda, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/215,007

(22) Filed: Aug. 22, 2011

(65) Prior Publication Data

US 2011/0303538 A1 Dec. 15, 2011

Related U.S. Application Data

(63) Continuation of application No. 12/843,607, filed on Jul. 26, 2010, now Pat. No. 8,168,052, which is a continuation of application No. 11/503,519, filed on Aug. 10, 2006, now Pat. No. 7,918,976, which is a continuation of application No. 10/639,181, filed on Aug. 11, 2003, now Pat. No. 7,090,756, which is a continuation of application No. 09/712,452, filed on Nov. 14, 2000, now Pat. No. 6,605,201.

(60) Provisional application No. 60/165,565, filed on Nov. 15, 1999.

(51) Int. Cl.
*C07F 15/00* (2006.01)
*G01N 27/327* (2006.01)

(52) U.S. Cl.
USPC .......... 204/403.14; 204/403.04; 525/161; 546/2; 548/101

(58) Field of Classification Search
USPC .......... 204/403.1, 403.04, 403.14; 526/161; 546/2; 548/101
See application file for complete search history.

(56) References Cited

U.S. PATENT DOCUMENTS

| | | |
|---|---|---|
| 5,262,035 A | 11/1993 | Gregg et al. |
| 5,262,305 A | 11/1993 | Heller et al. |
| 5,264,092 A | 11/1993 | Skotheim et al. |
| 5,264,104 A | 11/1993 | Gregg et al. |
| 5,264,105 A | 11/1993 | Gregg et al. |
| 5,320,725 A | 6/1994 | Gregg et al. |
| 5,356,786 A | 10/1994 | Heller et al. |
| 5,378,628 A | 1/1995 | Grätzel et al. |
| 5,393,903 A | 2/1995 | Grätzel et al. |
| 5,410,059 A | 4/1995 | Fraser et al. |
| 5,437,999 A | 8/1995 | Diebold et al. |
| 5,463,057 A | 10/1995 | Graetzel et al. |
| 5,589,326 A | 12/1996 | Deng et al. |
| 5,593,852 A | 1/1997 | Heller et al. |
| 5,665,222 A | 9/1997 | Heller et al. |
| 5,683,832 A | 11/1997 | Bonhote et al. |
| 5,789,592 A | 8/1998 | Graetzel et al. |
| 5,804,049 A | 9/1998 | Chan |
| 5,846,702 A | 12/1998 | Deng et al. |
| 5,965,380 A | 10/1999 | Heller et al. |
| 5,972,199 A | 10/1999 | Heller et al. |
| 6,083,710 A | 7/2000 | Heller et al. |
| 6,103,033 A | 8/2000 | Say et al. |
| 6,120,676 A | 9/2000 | Heller et al. |
| 6,121,009 A | 9/2000 | Heller |
| 6,134,461 A | 10/2000 | Say et al. |
| 6,143,164 A | 11/2000 | Heller et al. |
| 6,175,752 B1 | 1/2001 | Say et al. |
| 6,245,988 B1 | 6/2001 | Greatzel et al. |
| 6,262,264 B1 | 7/2001 | Buck et al. |
| 6,278,056 B1 | 8/2001 | Sugihara et al. |
| 6,294,062 B1 | 9/2001 | Buck et al. |
| 6,338,790 B1 | 1/2002 | Feldman et al. |
| 6,352,824 B1 | 3/2002 | Buck et al. |
| 6,605,200 B1 | 8/2003 | Mao |
| 6,605,201 B1 | 8/2003 | Mao |
| 6,616,819 B1 | 9/2003 | Liamos et al. |
| 6,746,582 B2 | 6/2004 | Heller et al. |
| 7,429,630 B2 | 9/2008 | Liu et al. |
| 2008/0035479 A1 | 2/2008 | Liu et al. |

FOREIGN PATENT DOCUMENTS

| | | |
|---|---|---|
| CA | 2464572 | 1/2004 |
| EP | 1 230 249 | 8/2002 |
| JP | 4-114012 | 4/1992 |

(Continued)

OTHER PUBLICATIONS

Casado, Carmen M., Moises Moran, Jose Losada, and Isabel Cuadrado. "Siloxane and organosilicon dimers, monomers, and polymers with amide-linked ferrocenyl moieties. synthesis, characterization, and redox properties." Inorganic Chemistry 34, No. 7 (1995): 1668-1680.*

Abruna, H. D. et al., "Rectifying Interfaces Using Two-Layer Films of Electrochemically Polymerized Vinylpyridine and Vinylbipyridine Complexes of Ruthenium and Iron on Electrodes," J. Am. Chem. Soc., vol. 103, No. 1, pp. 1-5 (Jan. 14, 1981).

Calvert et al., "Synthetic and Mechanistic Investigations of the Reductive Electrochemical Polymerization of Vinyl-Containing Complexes of Iron (II), Ruthenium(II), and Osmium(II)," Inorganic Chemistry, vol. 22, No. 15, 1983, pp. 2151-2162.

Cass, A. et al., "Ferricinum Ion as an Electron Acceptor for Oxido-Reductases," J. Electroanal. Chem., vol. 190, pp. 117-127 (1985).

Cass, A. et al., "Ferrocene-Mediated Enzyme Electrode for Amperometric Determination of Glucose", Anal. Chem., vol. 56, No. 4, pp. 667-671 (Apr. 1984).

(Continued)

*Primary Examiner* — Luan Van
*Assistant Examiner* — Maris R Kessel
(74) *Attorney, Agent, or Firm* — Edward J. Baba; Khin K. Chin; Bozicevic, Field & Francis LLP

(57) ABSTRACT

Novel transition metal complexes of iron, cobalt, ruthenium, osmium, and vanadium are described. The transition metal complexes can be used as redox mediators in enzyme based electrochemical sensors. In such instances, transition metal complexes accept electrons from, or transfer electrons to, enzymes at a high rate and also exchange electrons rapidly with the sensor. The transition metal complexes include at least one substituted or unsubstituted biimidazole ligand and may further include a second substituted or unsubstituted biimidazole ligand or a substituted or unsubstituted bipyridine or pyridylimidazole ligand. Transition metal complexes attached to polymeric backbones are also described.

18 Claims, No Drawings

(56) References Cited

FOREIGN PATENT DOCUMENTS

| | | |
|---|---|---|
| WO | WO 98/35225 | 8/1998 |
| WO | WO 99/03868 | 1/1999 |
| WO | WO 99/45375 | 9/1999 |
| WO | WO 99/45387 | 9/1999 |
| WO | WO 99/56613 | 11/1999 |
| WO | WO 99/59218 | 11/1999 |
| WO | WO 99/67628 | 12/1999 |
| WO | WO 00/20626 | 4/2000 |
| WO | WO 03/098731 | 11/2003 |

OTHER PUBLICATIONS

Chen, C.Y. et al., "A Biocompatible Needle-Type Glucose Sensor Based on Platinum-Electroplated Carbon Electrode", Applied Biochemistry and Biotechnology, vol. 36, pp. 211-226 (1992).
Chen, C.Y. et al., "Amperometric Needle-Type Glucose Sensor based on a Modified Platinum Electrode with Diminished Response to Interfering Materials", Analytica Chimica Acta, vol. 265, pp. 5-14 (1992).
Csoregi, E. et al., "Design, Characterization, and One-Point in Vivo Calibration of a Subcutaneously Implanted Glucose Electrode," Anal. Chem., vol. 66, No. 19, pp. 31313138 (Oct. 1, 1994).
Csoregi, E. et al., "On-Line Glucose Monitoring by Using Microdialysis Sampling and Amperometric Detection Based on "Wired" Glucose Oxidase in Carbon Paste," Mikrochim Acta., vol. 121, pp. 31-40 (1995).
Degani, Y. et al., "Direct Electrical Communication between Chemically Modified Enzymes and Metal Electrodes. 2. Methods for Bonding Electron-Transfer Relays to Glucose Oxidase and D-Amino-Acid Oxidase," J. Am. Chem. Soc., vol. 110, No. 8, pp. 2615-2620 (1988).
Degani, Y. et al., "Electrical Communication between Redox Centers of Glucose Oxidase and Electrodes via Electrostatically and Covalently Bound Redox Polymers," J. Am. Chem. Soc., vol. 111, pp. 23572358 (1989).
Degani, Y. et al., Direct Electrical Communication between Chemically Modified Enzymes and Metal Electrodes. 1. Electron Transfer from Glucose Oxidase to Metal Electrodes via Electron Relays, Bound Covalently to the Enzyme, J. Phys. Chem., vol. 91, No. 6, pp. 1285-1289 (1987).
Dicks, J. M., "Ferrocene modified polypyrrole with immobilised glucose oxidase and its application in amperometric glucose microbiosensors," Ann. Biol. clin., vol. 47, pp. 607-619 (1989).
Doherty, a.P. et al., "The Effect of the Nature of the Polymer Backbone on the Stability and the Analytical Response of Polymer-Modified Electrodes", Electroanalysis, vol. 7, No. 4, pp. 333-339 (1995).
Dupray et al. "Synthesis and Characterization of Amide-Derivatized, Polypyridyl-Based Metopolymers" Inorg. Chem. 1996, 35, pp. 6299-6307.
Fieselmann, B. et al., "Synthesis, Electron Paramagnetic Resonance, and Magnetic Studies on Binuclear Bis(.eta..sup.5 -cyclopentadienyl)titanium(III) Compounds with Bridging Pyrazolate, Biimidazolate, and Bibenzimidazolate Anions", Inorganic Chemistry, vol. 17, No. 8, pp. 2078-2084, 1978.
Fischer, H. et al., "Intramolecular Electron Transfer Mediated by 4,4'-Bipyridine and Related Bridging Groups", J. Am. Chem. Soc., vol. 98, No. 18, pp. 5512-5517 (Sep. 1, 1976).
Foulds, N. et al., "Enzyme Entrapment in Electrically Conducting Polymers," J. Chem. Soc., Faraday Trans 1., vol. 82, pp. 1259-1264 (1986).
Foulds, N. et al., "Immobilization of Glucose Oxidase in Ferrocene-Modified Pyrrole Polymers," Anal. Chem., vol. 60, No. 22, pp. 2473-2478 (Nov. 15, 1988).
Gholamkhass et al. "Evaluation of Electronic Interaction Matrix Elements for Photoinduced Electron Transfer Processes within Mixed-Valence Complexes" J. Phys. Chem. B 1997, 101, pp. 9010-9021.
Gregg, B. et al., "Cross-Linked Redox Gels Containing Glucose Oxidase for Amperometric Biosensor Applications," Analytical Chemistry, vol. 62, No. 3, pp. 258-263 (Feb. 1, 1990).

Gregg, B. et al., "Redox Polymer Films Containing Enzymes. 1. A Redox-Conducting Epoxy Cement: Synthesis, Characterization, and Electrocatalytic Oxidation of Hydroquinone," J. Phys. Chem., vol. 95, No. 15, pp. 5970-5975 (1991).
Haga, M., "Synthesis and Protonation-deprotonation Reactions of Ruthenium(II) Complexes Containing 2,2'-Bibenzimidazole and Related Ligands", Inorganica Chimica Acta, vol. 75, pp. 29-35 (1983).
Hale, P. et al., "A New Class of Amperometric Biosensor Incorporating a Polymeric Electron-Transfer Mediator," J. Am. Chem. Soc., vol. 111, No. 9, pp. 3482-3484 (1989).
Hedenmo et al. "Reagentless Amperometric Glucose Dehydrogenase Biosensor Based on Electrocatalytic Oxidation of NADH by Osmium Phenanthrolinedione" Analyst 1996, 121, pp. 1891-1895.
Heller, A., "Electrical Connection of Enzyme Redox Centers to Electrodes," J. Phys. Chem., vol. 96, No. 9, pp. 3579-3587 (1992).
Heller, a., "Electrical Wiring of Redox Enzymes," Acc. Chem. Res., vol. 23, No. 5, pp. 129-134 (1990).
Ianniello, R.M. et al "Immobilized Enzyme Chemically Modified Electrode as an Amperometric Sensor", Anal. Chem., vol. 53, No. 13, pp. 2090-2095 (Nov. 1981).
Ikeda, T. et al., "Glucose oxidase-immobilized benzoquinone-carbon paste electrode as a glucose sensor," Agric. Biol. Chem., vol. 49, No. 2, (1 page—Abstract only) (1985).
Jönsson, G. et al., "An Amperometric Glucose Sensor Made by Modification of a Graphite Electrode Surface with Immobilized Glucose Oxidase and Adsorbed Mediator", Biosensors, vol. 1, pp. 355-368 (1985).
Katakis, I. et al., "Electrostatic Control of the Electron Transfer Enabling Binding of Recombinant Glucose Oxidase and Redox Polyelectrolytes," J. Am. Chem. Soc., vol. 116, No. 8, pp. 3617-3618 (1994).
Katakis, I. et al., "L-.alpha.-Glycerophosphate and L-Lactate Electrodes Based on the Electrochemical "Wiring" of Oxidases," Analytical Chemistry, vol. 64, No. 9, pp. 1008-1013 (May 1, 1992).
Kenausis, G. et al., "'Wiring' of glucose oxidase and lactate oxidase within a hydrogel made with poly(vinly pyridine) complexed with [Os(4,4'-dimethoxy-2,2'-bipyridine).sub.2 Cl].sup.+/2 +," J. Chem. Soc., Faraday Trans., vol. 92, No. 20, pp. 4131-4136 (1996).
Maidan, R. et al., "Elimination of Electrooxidizable Interferant-Produced Currents in Amperometric Biosensors," Analytical Chemistry, vol. 64, No. 23, pp. 2889-2896 (Dec. 1, 1992).
Majumdar et al, "Biimidazole Complexes of $ML_2^{2+}$ [M=Ru or Os, L=2-(phenylazo)-pyridine]. Synthesis Structure and Redox Properties of Mono-and di-nuclear Complexes" J. Chem. Soc. Dalton Trans., 1998, pp. 1569-1574.
Ohara, T. et al., ""Wired" Enzyme Electrodes for Amperometric Determination of Glucose or Lactate in the Presence of Interfering Substances," Analytical Chemistry, vol. 66, No. 15, pp. 2451-2457 (Aug. 1, 1994).
Ohara, T. et al., "Glucose Electrodes Based on Cross-Linked [Os(bpy).sub.2 Cl].sup.+/2+Complexed Poly(1-vinylimadazole) Films," Analytical Chemistry, vol. 65, No. 23, pp. 3512-3516 (Dec. 1, 1993).
Ohara, T., "Osmium Bipyridyl Redox Polymers Used in Enzyme Electrodes," Platinum Metals Rev., vol. 39, No. 2, pp. 54-62 (Apr. 1995).
Orellana, et al. "Spectroscopic, Electrochemical, and Kinetic Characterization of New Ruthenium(II) Tris-chelates Containing Five-Membered Heterocyclic Moieties" Helvetica Chimica Acta, 1987, vol. 70, No. 8, p. 2073-2086.
Park et al., "Sol-Gel-based Amperometric Glucose Biosensor Incorporating an Osmium Redox Polymer as Mediator," Analytical Communications, 33:271-273 (Aug. 1996).
Pickup, J. et al., "Potentially-implantable, amperometric glucose sensors with mediated electron transfer: improving the operating stability," Biosensors, vol. 4, No. 2, (1 page—Abstract only) (1989).
Pishko, M. et al., "Amperometric Glucose Microelectrodes Prepared Through Immobilization of Glucose Oxidase in Redox Hydrogels", Anal. Chem., vol. 63, No. 20, pp. 2268-2272 (Oct. 15, 1991).
Pollak, A. et al., "Enzyme Immobilization by Condensation Copolymerization into Cross-Linked Polyacrylamide Gels,"J. Am. Chem. Soc., vol. 102, No. 20, pp. 6324-6336 (1980).

(56) References Cited

OTHER PUBLICATIONS

Reeder, K. et al., "Solution-State Spin-Equilibrium Properties of the Tris[2-(2-pyridyl)benzimidazole]iron(II) and Tris[2-(2-pyridyl)benzimidazole]iron(II) Cations", Inorganic Chemistry, vol. 17, No. 4, pp. 1071-1075 (1978).

Sasso, S. et al., "Electropolymerized 1,2-Diaminobenzene as a Means to Prevent Interferences and Fouling and to Stabilize Immobilized Enzyme in Electrochemical Biosensors", Anal. Chem., vol. 62, No. 11, pp. 1111-1117 (Jun. 1, 1990).

Schalkhammer, T. et al., "Electrochemical Glucose Sensors on Permselective Non-conducting Substituted Pyrrole Polymers", Sensors and Actuators, vol. B4, pp. 273-281 (1991).

Schmehl et al., "The Effect of Redox Site Concentration on the Rate of Mediated Oxidation of Solution Substrates by a Redox Copolymer Film," J. Electroanal. Chem. 152, 1983, pp. 97-109.

Sugiyarto, et al. "Structural, Magnetic and Mossbauer Studies of Bis(2,6-bis(pyrazol-3-yl)pyridine)iron(II) Triflate and its Hydrates" Australian Journal of Chemistry, 1987, vol. 40, No. 5, p. 775-783.

Surridge et al., Electron and Counterion Diffusion Constants in Mixed-Valent Polymeric Osmium Bipyridine Films, The Journal of Physical Chemistry, vol. 98, No. 3, 1994, pp. 917-923.

Surridge et al., Site Dilution of Osmium Polypyridine Complexes in Three Electron-Hopping Conductive Polymer Films on Electrodes by Electrochemical Copolymerization of Osmium with Ruthenium and with Zinc Complexes,' Inorganic Chemistry, vol. 29, No. 24, 1990, pp. 4950.

Taylor, C. et al., "'Wiring' of glucose oxidase within a hydrogel made with polyvinyl imidazole complexed with [(Os-4,4'-dimethoxy-2,2'-bipyridine)Cl].sup.+/2+," Journal of Electroanalytical Chemistry, vol. 396, pp. 511-515 ()1995).

Trojanowicz, M. et al., "Enzyme Entrapped Polypyrrole Modified Electrode for Flow-Injection Determination of Glucose," Biosensors & Bioelectronics, vol. 5, pp. 149-156 (1990).

Ye, L. et al., "High Current Density "Wired" Quinoprotein Glucose Dehydrogenase Electrode," Anal. Chem., vol. 65, No. 3, pp. 238-241 (Feb. 1, 1993).

Yildiz, A., "Evaluation of an Improved Thin-Layer Electrode", Analytical Chemistry vol. 40, No. 7, pp. 1018-1024 (Jun. 1968).

Yu et al, "Synthesis, Metal Complex Formation, and Electronic Properties of a Novel Conjugate Polymer with a Tridentate 2,6-Bis(benzimidazol-2-yl)pyridine Ligand" Macromolecules, 1999, 32, pp. 5251-5256.

* cited by examiner

REDOX POLYMERS

RELATED APPLICATIONS

This application is a continuation of U.S. patent application Ser. No. 12/843,607, filed on Jul. 26, 2010, issued as U.S. Pat. No. 8,168,052, which is a continuation of U.S. patent application Ser. No. 11/503,519, filed on Aug. 10, 2006, issued as U.S. Pat. No. 7,918,976, which is a continuation of U.S. patent application Ser. No. 10/639,181, filed Aug. 11, 2003, issued as U.S. Pat. No. 7,090,756, which is a continuation of U.S. patent application Ser. No. 09/712,452, filed Nov. 14, 2000, issued as U.S. Pat. No. 6,605,201, which claims benefit of U.S. Provisional Patent Application Ser. No. 60/165,565, filed Nov. 15, 1999, which are incorporated herein by reference.

FIELD OF THE INVENTION

This invention relates to transition metal complexes with at least one bidentate ligand containing at least one imidazole ring. In addition, the invention relates to the preparation of the transition metal complexes and to the use of the transition metal complexes as redox mediators.

BACKGROUND OF THE INVENTION

Enzyme based electrochemical sensors are widely used in the detection of analytes in clinical, environmental, agricultural and biotechnological applications. Analytes that can be measured in clinical assays of fluids of the human body include, for example, glucose, lactate, cholesterol, bilirubin and amino acids. Levels of these analytes in biological fluids, such as blood, are important for the diagnosis and the monitoring of diseases.

Electrochemical assays are typically performed in cells with two or three electrodes, including at least one measuring or working electrode and one reference electrode. In three electrode systems, the third electrode is a counter-electrode. In two electrode systems, the reference electrode also serves as the counter-electrode. The electrodes are connected through a circuit, such as a potentiostat. The measuring or working electrode is a non-corroding carbon or metal conductor. Upon passage of a current through the working electrode, a redox enzyme is electrooxidized or electroreduced. The enzyme is specific to the analyte to be detected, or to a product of the analyte. The turnover rate of the enzyme is typically related (preferably, but not necessarily, linearly) to the concentration of the analyte itself, or to its product, in the test solution.

The electrooxidation or electroreduction of the enzyme is often facilitated by the presence of a redox mediator in the solution or on the electrode. The redox mediator assists in the electrical communication between the working electrode and the enzyme. The redox mediator can be dissolved in the fluid to be analyzed, which is in electrolytic contact with the electrodes, or can be applied within a coating on the working electrode in electrolytic contact with the analyzed solution. The coating is preferably not soluble in water, though it may swell in water. Useful devices can be made, for example, by coating an electrode with a film that includes a redox mediator and an enzyme where the enzyme is catalytically specific to the desired analyte, or its product. In contrast to a coated redox mediator, a diffusional redox mediator, which can be soluble or insoluble in water, functions by shuttling electrons between, for example, the enzyme and the electrode. In any case, when the substrate of the enzyme is electrooxidized, the redox mediator transports electrons from the substrate-reduced enzyme to the electrode; when the substrate is electroreduced, the redox mediator transports electrons from the electrode to the substrate-oxidized enzyme.

Recent enzyme based electrochemical sensors have employed a number of different redox mediators such as monomeric ferrocenes, quinoid-compounds including quinines (e.g., benzoquinones), nickel cyclamates, and ruthenium ammines. For the most part, these redox mediators have one or more of the following limitations: the solubility of the redox mediators in the test solutions is low, their chemical, light, thermal, or pH stability is poor, or they do not exchange electrons rapidly enough with the enzyme or the electrode or both. Additionally, the redox potentials of many of these reported redox mediators are so oxidizing that at the potential where the reduced mediator is electrooxidized on the electrode, solution components other than the analyte are also electrooxidized; in other cases they are so reducing that solution components, such as, for example, dissolved oxygen are also rapidly electroreduced. As a result, the sensor utilizing the mediator is not sufficiently specific.

SUMMARY OF THE INVENTION

The present invention is directed to novel transition metal complexes. The present invention is also directed to the use of the complexes as redox mediators. The preferred redox mediators typically exchange electrons rapidly with enzymes and electrodes, are stable, and have a redox potential that is tailored for the electrooxidation of analytes, exemplified by glucose.

One embodiment of the invention is a transition metal complex having the formula:

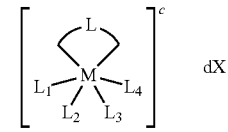

M is cobalt, ruthenium, osmium, or vanadium. L is selected from the group consisting of:

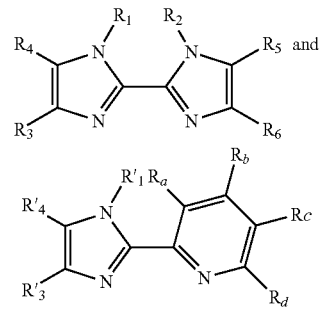

$R_1$, $R_2$, and $R'_1$ are independently substituted or unsubstituted alkyl, alkenyl, or aryl groups. $R_3$, $R_4$, $R_5$, $R_6$, $R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino, alkylthio, alkenyl, aryl, or alkyl. c is an integer selected from −1 to −5 or +1 to +5 indicating a positive or negative charge. X represents at least one counter ion and d is an integer from 1 to 5 representing the number of counter ions, X. $L_1, L_2, L_3$ and $L_4$ are other ligands.

Another embodiment is a redox mediator having the formula:

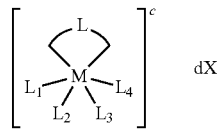

M is iron, cobalt, ruthenium, osmium, or vanadium. L is a bidentate ligand comprising at least one imidazole ring. c is an integer selected from −1 to −5 or +1 to +5 indicating a positive or negative charge. X represents at least one counter ion and d is an integer from 1 to 5 representing the number of counter ions, X. $L_1, L_2, L_3$ and $L_4$ are other ligands.

Another embodiment is a sensor that includes the redox polymer, a working electrode, and a counter electrode. The redox polymer is disposed proximate to the working electrode.

Yet another embodiment is a polymer that includes a polymeric backbone and a transition metal complex having the following formula:

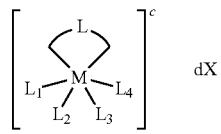

M is iron, cobalt, ruthenium, osmium, or vanadium. L is a bidentate ligand comprising at least one imidazole ring. c is an integer selected from −1 to −5 or +1 to +5 indicating a positive or negative charge. X represents at least one counter ion and d is an integer from 1 to 5 representing the number of counter ions, X. $L_1, L_2, L_3$ and $L_4$ are other ligands where at least one of L, $L_1, L_2, L_3$ and $L_4$ couples to the polymeric backbone.

The redox polymers are generally capable of carrying electrons between an enzyme and an electrode. The polymers can be useful in electrochemical biosensors. One embodiment is a polymeric transition metal complex that includes a polymeric backbone, a plurality of spacers, and a plurality of transition metal complexes. Each of the spacers is covalently coupled to and extending from the polymeric backbone and includes at least one non-cyclic functional group selected from the group consisting of —$(CR^rR^s)$—, —O—, —S—, —C(O)O—, —$S(O)_2NR^k$—, —$OC(O)NR^m$—, —OC(S)$NR^n$—, —$C(O)NR^t$—, —$NR^u$—, —$CR^v=N$—O—, —$CR^w=NNR^x$—, and —$(SiR^yR^z)$—, where $R^r$ and $R^s$ are independently hydrogen, chlorine, fluorine, or substituted or unsubstituted alkyl, alkoxy, alkenyl, or alkynyl and $R^k, R^m, R^n, R^t, R^u, R^v, R^w, R^x, R^y$, and $R^z$ are independently hydrogen or substituted or unsubstituted alkyl. Each of the transition metal complexes has the formula:

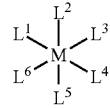

M is osmium, ruthenium, vanadium, cobalt, or iron. $L^1$ is a ligand that includes a heterocycle and is coordinatively bound to M via a heteroatom of the heterocycle. $L^2, L^3, L^4, L^5$, and $L^6$ are ligands, where each of $L^1, L^2, L^3, L^4, L^5$, and $L^6$ is independently a monodentate ligand or combined with at least one other ligand to form a multidentate ligand. At least one of $L^1, L^2, L^3, L^4, L^5$, and $L^6$ is covalently coupled to one of the spacers.

Another embodiment is a polymeric transition metal complex that includes a reaction product of a) a polymer having a polymeric backbone and a plurality of pendant groups extending from the polymeric backbone, where at least a portion of the pendant groups have a reactive group and b) a plurality of transition metal complexes, each transition metal complex having the formula:

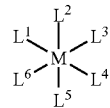

M is osmium, ruthenium, vanadium, cobalt, or iron. $L^1$ is a ligand comprising a heterocycle and coordinatively bound to M via a heteroatom of the heterocycle. $L^2, L^3, L^4, L^5$, and $L^6$ are ligands, where each of $L^1, L^2, L^3, L^4, L^5$, and $L^6$ is independently a monodentate ligand or combined with at least one other ligand to form a multidentate ligand. At least one of $L^1, L^2, L^3, L^4, L^5$, and $L^6$ includes a reactive group that is capable of reacting with one of the reactive groups of the polymer.

Yet another embodiment is a polymeric transition metal complex that includes a polymeric backbone, a plurality of spacers, and a plurality of transition metal complexes. Each spacer is covalently coupled to and extends from the polymeric backbone and includes a flexible chain of at least four atoms. Each transition metal complex has the formula:

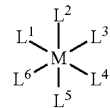

M is osmium, ruthenium, vanadium, cobalt, or iron. $L^1$ is a ligand comprising a heterocycle and coordinatively bound to M via a heteroatom of the heterocycle. $L^2, L^3, L^4, L^5$, and $L^6$ are ligands, where each of $L^1, L^2, L^3, L^4, L^5$, and $L^6$ is independently a monodentate ligand or combined to form one or more multidentate ligands. At least one of $L^1, L^2, L^3, L^4, L^5$, and $L^6$ is covalently coupled to one of the spacers.

Another embodiment of the invention is a redox mediator that includes any of the polymeric transition metal complexes described above.

Yet another embodiment is a sensor that includes the redox mediator, a working electrode, and a counter electrode. The redox mediator is disposed proximate to the working electrode. Preferably, the redox mediator is disposed on the working electrode. More preferably, the redox mediator is non-leachably disposed on the working electrode.

DETAILED DESCRIPTION

When used herein, the following definitions define the stated term:

The term "alkyl" includes linear or branched, saturated aliphatic hydrocarbons. Examples of alkyl groups include methyl, ethyl, n-propyl, isopropyl, n-butyl, tert-butyl and the like. Unless otherwise noted, the term "alkyl" includes both alkyl and cycloalkyl groups.

The term "alkoxy" describes an alkyl group joined to the remainder of the structure by an oxygen atom. Examples of alkoxy groups include methoxy, ethoxy, n-propoxy, isopropoxy, butoxy, tert-butoxy, and the like. In addition, unless otherwise noted, the term 'alkoxy' includes both alkoxy and cycloalkoxy groups.

The term "alkenyl" describes an unsaturated, linear or branched aliphatic hydrocarbon having at least one carbon-carbon double bond. Examples of alkenyl groups include ethenyl, 1-propenyl, 2-propenyl, 1-butenyl, 2-methyl-1-propenyl, and the like.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

A "substituted" functional group (e.g., substituted alkyl, alkenyl, or alkoxy group) includes at least one substituent selected from the following: halogen, alkoxy, mercapto, aryl, alkoxycarbonyl, alkylaminocarbonyl, dialkylaminocarbonyl, —OH, —NH$_2$, alkylamino, dialkylamino, trialkylammonium, alkanoylamino, arylcarboxamido, hydrazino, alkylthio, alkenyl, and reactive groups.

A "biological fluid" is any body fluid or body fluid derivative in which the analyte can be measured, for example, blood, interstitial fluid, plasma, dermal fluid, sweat, and tears.

An "electrochemical sensor" is a device configured to detect the presence of or measure the concentration or amount of an analyte in a sample via electrochemical oxidation or reduction reactions. These reactions typically can be transduced to an electrical signal that can be correlated to an amount or concentration of analyte.

A "redox mediator" is an electron transfer agent for carrying electrons between an analyte or an analyte-reduced or analyte-oxidized enzyme and an electrode, either directly, or via one or more additional electron transfer agents.

"Electrolysis" is the electrooxidation or electroreduction of a compound either directly at an electrode or via one or more electron transfer agents (e.g., redox mediators or enzymes).

The term "reference electrode" includes both a) reference electrodes and b) reference electrodes that also function as counter electrodes (i.e., counter/reference electrodes), unless otherwise indicated.

The term "counter electrode" includes both a) counter electrodes and b) counter electrodes that also function as reference electrodes (i.e., counter/reference electrodes), unless otherwise indicated.

The term "flexible chain" refers to a saturated C4 to C24 chain where, optionally, one or more of the carbon atoms are replaced by heteroatoms (such as, for example, oxygen, sulfur, or nitrogen) as part of, for example, an ether, thioether, or amine group. The chain can be substituted or unsubstituted.

Generally, the present invention relates to transition metal complexes of iron, cobalt, ruthenium, osmium, and vanadium having at least one bidentate ligand containing an imidazole ring. The invention also relates to the preparation of the transition metal complexes and to the use of the transition metal complexes as redox mediators. In at least some instances, the transition metal complexes have one or more of the following characteristics: redox potentials in a particular range, the ability to exchange electrons rapidly with electrodes, the ability to rapidly transfer electrons to or rapidly accept electrons from an enzyme to accelerate the kinetics of electrooxidation or electroreduction of an analyte in the presence of an enzyme or another analyte-specific redox catalyst. For example, a redox mediator may accelerate the electrooxidation of glucose in the presence of glucose oxidase or PQQ-glucose dehydrogenase, a process that can be useful for the selective assay of glucose in the presence of other electrochemically oxidizable species. Compounds having the formula 1 are examples of transition metal complexes of the present invention.

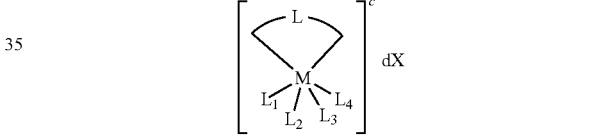

M is a transition metal and is typically iron, cobalt, ruthenium, osmium, or vanadium. Ruthenium and osmium are particularly suitable for redox mediators.

L is a bidentate ligand containing at least one imidazole ring. One example of L is a 2,2'-biimidazole having the following structure 2:

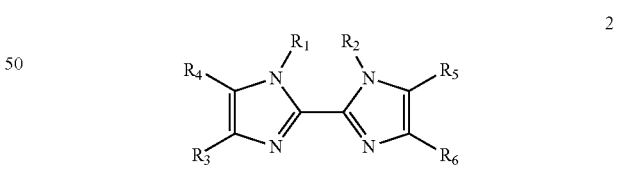

$R_1$ and $R_2$ are substituents attached to two of the 2,2'-biimidazole nitrogens and are independently substituted or unsubstituted alkyl, alkenyl, or aryl groups. Generally, $R_1$ and $R_2$ are unsubstituted C1 to C12 alkyls. Typically, $R_1$ and $R_2$ are unsubstituted C1 to C4 alkyls. In some embodiments, both $R_1$ and $R_2$ are methyl.

$R_3$, $R_4$, $R_5$, and $R_6$ are substituents attached to carbon atoms of the 2,2'-biimidazole and are independently —H, —F, —Cl, —Br, —I, —NO$_2$, —CN, —CO$_2$H, —SO$_3$H, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_3$ and $R_4$ in combination or $R_5$ and $R_6$ in combination independently form a saturated or unsaturated 5- or 6-membered ring. An example of this is a 2,2'-bibenzoimidazole derivative. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Generally, $R_3$, $R_4$, $R_5$, and $R_6$ are independently —H or unsubstituted alkyl groups. Typically, $R_3$, $R_4$, $R_5$, and $R_6$ are —H or unsubstituted C1 to C12 alkyls. In some embodiments, $R_3$, $R_4$, $R_5$, and $R_6$ are all —H.

Another example of L is a 2-(2-pyridyl)imidazole having the following structure 3:

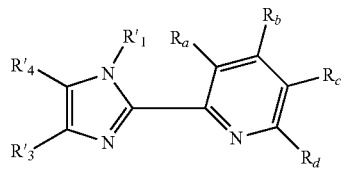

3

$R'_1$ is a substituted or unsubstituted aryl, alkenyl, or alkyl. Generally, $R'_1$ is a substituted or unsubstituted C1-C12 alkyl. $R'_1$ is typically methyl or a C1-C12 alkyl that is optionally substituted with a reactive group.

$R'_3$, $R'_4$, $R_a$, $R_b$, $R_c$, and $R_d$ are independently —H, —F, —Cl, —Br, —I, —NO$_2$, —CN, —CO$_2$H, —SO$_3$H, —NHNH$_2$, —SH, alkoxylcarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxylamino, alkylthio, alkenyl, aryl, or alkyl. Alternatively, $R_c$ and $R_d$ in combination or $R'_3$ and $R'_4$ in combination can form a saturated or unsaturated 5- or 6-membered ring. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Generally, $R'_3$, $R'_4$, $R_a$, $R_b$, $R_c$ and $R_d$ are independently —H or unsubstituted alkyl groups. Typically, $R_a$ and $R_c$ are —H and $R'_3$, $R'_4$, $R_b$, and $R_d$ are —H or methyl.

c is an integer indicating the charge of the complex. Generally, c is an integer selected from −1 to −5 or +1 to +5 indicating a positive or negative charge. For a number of osmium complexes, c is +2 or +3.

X represents counter ion(s). Examples of suitable counter ions include anions, such as halide (e.g., fluoride, chloride, bromide or iodide), sulfate, phosphate, hexafluorophosphate, and tetrafluoroborate, and cations (preferably, monovalent cations), such as lithium, sodium, potassium, tetralkylammonium, and ammonium. Preferably, X is a halide, such as chloride. The counter ions represented by X are not necessarily all the same.

d represents the number of counter ions and is typically from 1 to 5.

$L_1$, $L_2$, $L_3$ and $L_4$ are ligands attached to the transition metal via a coordinative bond. $L_1$, $L_2$, $L_3$ and $L_4$ can be monodentate ligands or, in any combination, bi-, ter-, or tetradentate ligands For example, $L_1$, $L_2$, $L_3$ and $L_4$ can combine to form two bidentate ligands such as, for example, two ligands selected from the group of substituted and unsubstituted 2,2'-biimidazoles, 2-(2-pyridyl)imidizoles, and 2,2'-bipyridines Examples of other $L_1$, $L_2$, $L_3$ and $L_4$ combinations of the transition metal complex include:

(A) $L_1$ is a monodentate ligand and $L_2$, $L_3$ and $L_4$ in combination form a terdentate ligand;

(B) $L_1$ and $L_2$ in combination are a bidentate ligand, and $L_3$ and $L_4$ are the same or different monodentate ligands;

(C) $L_1$ and $L_2$ in combination, and $L_3$ and $L_4$ in combination form two independent bidentate ligands which can be the same or different; and (D) $L_1$, $L_2$, $L_3$ and $L_4$ in combination form a tetradentate ligand.

Examples of suitable monodentate ligands include, but are not limited to, —F, —Cl, —Br, —I, —CN, —SCN, —OH, H$_2$O, NH$_3$, alkylamine, dialkylamine, trialkylamine, alkoxy or heterocyclic compounds. The alkyl or aryl portions of any of the ligands are optionally substituted by —F, —Cl, —Br, —I, alkylamino, dialkylamino, trialkylammonium (except on aryl portions), alkoxy, alkylthio, aryl, or a reactive group. Any alkyl portions of the monodentate ligands generally contain 1 to 12 carbons. More typically, the alkyl portions contain 1 to 6 carbons. In other embodiments, the monodentate ligands are heterocyclic compounds containing at least one nitrogen, oxygen, or sulfur atom. Examples of suitable heterocyclic monodentate ligands include imidazole, pyrazole, oxazole, thiazole, pyridine, pyrazine and derivatives thereof. Suitable heterocyclic monodentate ligands include substituted and unsubstituted imidazole and substituted and unsubstituted pyridine having the following general formulas 4 and 5, respectively:

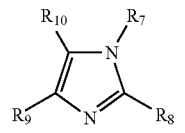

4

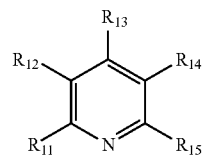

5

With regard to formula 4, $R_7$ is generally a substituted or unsubstituted alkyl, alkenyl, or aryl group. Typically, $R_7$ is a substituted or unsubstituted C1 to C12 alkyl or alkenyl. The substitution of inner coordination sphere chloride anions by imidazoles does not typically cause a large shift in the redox potential in the oxidizing direction, differing in this respect from substitution by pyridines, which typically results in a large shift in the redox potential in the oxidizing direction.

$R_8$, $R_9$ and $R_{10}$ are independently —H, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino, alkylthio, alkenyl, aryl, or alkyl. Alternatively, $R_9$ and $R_{10}$, in combination, form a fused 5 or 6-membered ring that is saturated or unsaturated. The alkyl portions of the substituents generally contain 1 to 12 carbons and typically contain 1 to 6 carbon atoms. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. In some embodiments, $R_8$, $R_9$ and $R_{10}$ are —H or substituted or unsubstituted alkyl. Preferably, $R_9$, $R_9$ and $R_{10}$ are —H.

With regard to Formula 5, $R_{11}$, $R_{12}$, $R_{13}$, $R_{14}$ and $R_{15}$ are independently —H, —F, —Cl, —Br, —I, —NO$_2$, —CN, —CO$_2$H, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxyamino, alkylthio, alkenyl, aryl, or alkyl. The alkyl or aryl portions of any of the substituents are optionally substituted by —F, —Cl, —Br, —I, alkylamino, dialkylamino, trialkylammonium (except for aryl portions), alkoxy, alkylthio, aryl, or a reactive group. Generally, $R_{11}$, $R_{12}$, $R_{13}$, $R_{14}$ and $R_{15}$ are —H, methyl, C1-C2 alkoxy, C1-C2 alkylamino, C2-C4 dialkylamino, or a C1-C6 lower alkyl substituted with a reactive group.

One example includes $R_{11}$ and $R_{15}$ as —H, $R_{12}$ and $R_{14}$ as the same and —H or methyl, and $R_{13}$ as —H, C1 to C12 alkoxy, —NH$_2$, C1 to C12 alkylamino, C2 to C24 dialkylamino, hydrazino, C1 to C12 alkylhydrazino, hydroxylamino, C1 to C12 alkoxyamino, C1 to C12 alkylthio, or C1 to C12 alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Examples of suitable bidentate ligands include, but are not limited to, amino acids, oxalic acid, acetylacetone, diaminoalkanes, ortho-diaminoarenes, 2,2'-biimidazole, 2,2'-bioxazole, 2,2'-bithiazole, 2-(2-pyridyl)imidazole, and 2,2'-bipyridine and derivatives thereof. Particularly suitable bidentate ligands for redox mediators include substituted and unsubstituted 2,2'-biimidazole, 2-(2-pyridyl)imidazole and 2,2'-bipyridine. The substituted 2,2' biimidazole and 2-(2-pyridyl)imidazole ligands can have the same substitution patterns described above for the other 2,2'-biimidazole and 2-(2-pyridyl)imidazole ligand. A 2,2'-bipyridine ligand has the following general formula 6:

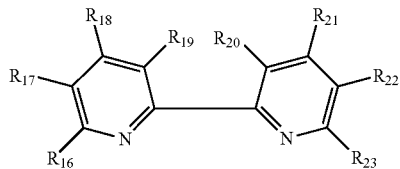

6

$R_{16}$, $R_{17}$, $R_{18}$, $R_{19}$, $R_{20}$, $R_{21}$, $R_{22}$ and $R_{23}$ are independently —H, —F, —Cl, —Br, —I, —NO$_2$, —CN, —CO$_2$H, —SO$_3$H, —NHNH$_2$, —SH, aryl, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxylamino, alkylthio, alkenyl, or alkyl. Typically, the alkyl and alkoxy portions are C1 to C12. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Specific examples of suitable combinations of $R_{16}$, $R_{17}$, $R_{18}$, $R_{19}$, $R_{20}$, $R_{21}$, $R_{22}$ and $R_{23}$ include $R_{16}$ and $R_{23}$ as H or methyl; $R_{17}$ and $R_{22}$ as the same and —H or methyl; and $R_{19}$ and $R_{20}$ as the same and —H or methyl. An alternative combination is where one or more adjacent pairs of substituents $R_{16}$ and $R_{17}$, on the one hand, and $R_{22}$ and $R_{23}$, on the other hand, independently form a saturated or unsaturated 5- or 6-membered ring. Another combination includes $R_{19}$ and $R_{20}$ forming a saturated or unsaturated five or six membered ring.

Another combination includes $R_{16}$, $R_{17}$, $R_{19}$, $R_{20}$, $R_{22}$ and $R_{23}$ as the same and —H and $R_{18}$ and $R_{21}$ as independently —H, alkoxy, —NH$_2$, alkylamino, dialkylamino, alkylthio, alkenyl, or alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. As an example, $R_{18}$ and $R_{21}$ can be the same or different and are —H, C1-C6 alkyl, C1-C6 amino, C1 to C12 alkylamino, C2 to C12 dialkylamino, C1 to C12 alkylthio, or C1 to C12 alkoxy, the alkyl portions of any of the substituents are optionally substituted by a —F, —Cl, —Br, —I, aryl, C2 to C12 dialkylamino, C3 to C18 trialkylammonium, C1 to C6 alkoxy, C1 to C6 alkylthio or a reactive group.

Examples of suitable terdentate ligands include, but are not limited to, diethylenetriamine, 2,2',2"-terpyridine, 2,6-bis(N-pyrazolyl)pyridine, and derivatives of these compounds. 2,2',2"-terpyridine and 2,6-bis(N-pyrazolyl)pyridine have the following general formulas 7 and 8 respectively:

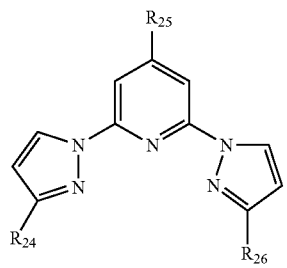

7

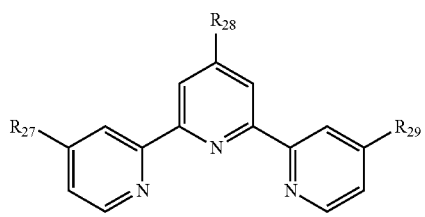

8

With regard to formula 7, $R_{24}$, $R_{25}$ and $R_{26}$ are independently —H or substituted or unsubstituted C1 to C12 alkyl. Typically, $R_{24}$, $R_{25}$ and $R_{26}$ are —H or methyl and, in some embodiments, $R_{24}$ and $R_{26}$ are the same and are —H. Other substituents at these or other positions of the compounds of formulas 7 and 8 can be added.

With regard to formula 8, $R_{27}$, $R_{28}$ and $R_{29}$ are independently —H, —F, —Cl, —Br, —I, —NO$_2$, —CN, —CO$_2$H, —SO$_3$H, —NHNH$_2$, —SH, alkoxycarbonyl, alkylaminocarbonyl, dialkylaminocarbonyl, —OH, alkoxy, —NH$_2$, alkylamino, dialkylamino, alkanoylamino, arylcarboxamido, hydrazino, alkylhydrazino, hydroxylamino, alkoxylamino, alkylthio, alkenyl, aryl, or alkyl. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. Typically, the alkyl and alkoxy groups are C1 to C12 and, in some embodiments, $R_{27}$ and $R_{29}$ are the same and are —H.

Examples of suitable tetradentate ligands include, but are not limited to, triethylenetriamine, ethylenediaminediacetic acid, tetraaza macrocycles and similar compounds as well as derivatives thereof.

Examples of suitable transition metal complexes are illustrated using Formula 9 and 10:

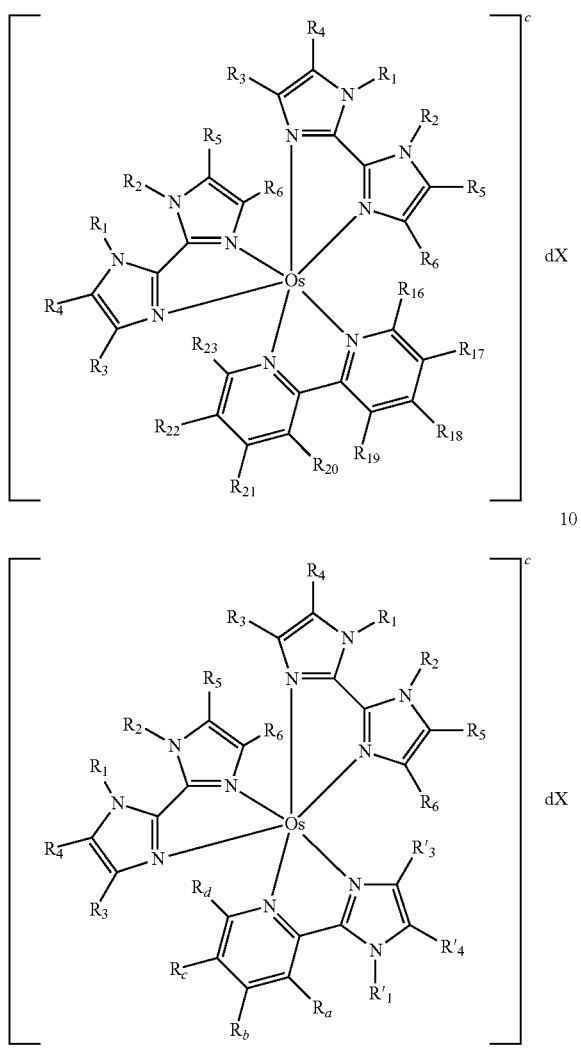

With regard to transition metal complexes of formula 9, the metal osmium is complexed to two substituted 2,2'-biimidazole ligands and one substituted or unsubstituted 2,2'-bipyridine ligand. $R_1$, $R_2$, $R_3$, $R_4$, $R_5$, $R_6$, $R_{16}$, $R_{17}$, $R_{18}$, $R_{19}$, $R_{20}$, $R_{21}$, $R_{22}$, $R_{23}$, c, d, and X are the same as described above.

In one embodiment, $R_1$ and $R_2$ are methyl; $R_3$, $R_4$, $R_5$, $R_6$, $R_{16}$, $R_{17}$, $R_{19}$, $R_{20}$, $R_{22}$ and $R_{23}$ are —H; and $R_{18}$ and $R_{21}$ are the same and are —H, methyl, or methoxy. Preferably, $R_{18}$ and $R_{21}$ are methyl or methoxy.

In another embodiment, $R_1$ and $R_2$ are methyl; $R_3$, $R_4$, $R_5$, $R_6$, $R_{16}$, $R_{17}$, $R_{18}$, $R_{19}$, $R_{20}$, $R_{22}$ and $R_{23}$ are —H; and $R_{21}$ is halo, C1 to C12 alkoxy, C1 to C12 alkylamino, or C2 to C24 dialkylamino. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group. For example, $R_{21}$ is a C1 to C12 alkylamino or C2 to C24 dialkylamino, the alkyl portion(s) of which are substituted with a reactive group, such as a carboxylic acid, activated ester, or amine. Typically, the alkylamino group has 1 to 6 carbon atoms and the dialkylamino group has 2 to 8 carbon atoms.

With regard to transition metal complexes of formula 10, the metal osmium is complexed to two substituted 2,2'-biimidazole ligands and one substituted or unsubstituted 2-(2-pyridyl)imidazole ligand. $R_1$, $R_2$, $R_3$, $R_4$, $R_5$, $R_6$, $R'_1$, $R'_3$, $R'_4$, $R_a$, $R_b$, $R_c$, $R_d$, c, d, and X are the same as described above.

In one embodiment, $R_1$ and $R_2$ are methyl; $R_3$, $R_4$, $R_5$, $R_6$, $R'_3$, $R'_4$ and $R_d$ are independently —H or methyl; $R_a$ and $R_c$ are the same and are —H; and $R_b$ is C1 to C12 alkoxy, C1 to C12 alkylamino, or C2 to C24 dialkylamino. The alkyl or aryl portions of any of the substituents are optionally substituted by —F, —Cl, —Br, —I, alkylamino, dialkylamino, trialkylammonium (except on aryl portions), alkoxy, alkylthio, aryl, or a reactive group.

Typically, each of the transition metal complexes has the formula:

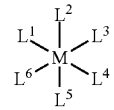

M is a transition metal and is typically osmium, ruthenium, vanadium, cobalt, or iron. $L^1$, $L^2$, $L^3$, $L^4$, $L^5$, and $L^6$ are ligands and are independently monodentate ligands or two or more of the ligands can be combined to form one or more multidentate ligands. $L^1$, in particular, is a ligand that includes a heterocycle and is coordinatively bound to M via a heteroatom of the heterocycle. At least one of $L^1$, $L^2$, $L^3$, $L^4$, $L^5$, and $L^6$ is covalently coupled to one of the spacers.

Any combination of monodentate and multidentate ligands can be used. For example, $L^2$, $L^3$, $L^4$, $L^5$, and $L^6$ can combine to form three bidentate ligands such as, for example, three bidentate ligands selected from substituted and unsubstituted 2,2'-biimidazoles, 2-(2-pyridyl)imidazoles, and 2,2'-bipyridines. Examples of other combinations of $L^2$, $L^3$, $L^4$, $L^5$, and $L^6$ include:

(A) Two monodentate ligands and two bidentate ligands;

(B) Four monodentate ligands and one bidentate ligand;

(C) Three monodentate ligands and one tridentate ligand;

(D) One monodentate ligand, one bidentate ligand, and one tridentate ligand;

(E) Two monodentate ligands and one tetradentate ligand; and (F) One bidentate ligand and one tetradentate ligand.

A list of specific examples of preferred transition metal complexes with respective redox potentials is shown in Table 1.

TABLE 1

Redox Potentials of Selected Transition Metal Complexes

| Complex | Structure | $E_{1/2}$(vs Ag/AgCl)/mV* |
|---|---|---|
| I | [Os(1,1'-dimethyl-2,2'-biimidazole)$_2$(4-dimethylamino-2,2'-bipyridine)]Cl$_3$ | −110 |
| II | [Os(1,1'-dimethyl-2,2'-biimidazole)$_2$(4-methylamino-2,2'-bipyridine)]Cl$_3$ | −100 |
| III | [Os(1,1'-dimethyl-2,2'-biimidazole)$_2$(4-bromo-2,2'-bipyridine)]Cl$_3$ | 128 |

TABLE 1-continued
Redox Potentials of Selected Transition Metal Complexes
| Complex | Structure | $E_{1/2}$(vs Ag/AgCl)/mV* |
|---|---|---|
| IV | 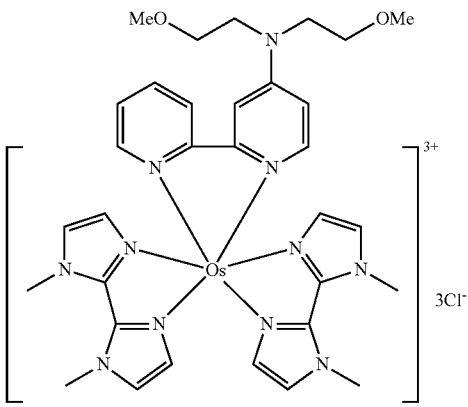 [Os(1,1'-dimethyl-2,2'-biimidazole)$_2$(4-di(2-methoxyethyl)amino-2,2'-bipyridine)]Cl$_3$ | −86 |
| V | 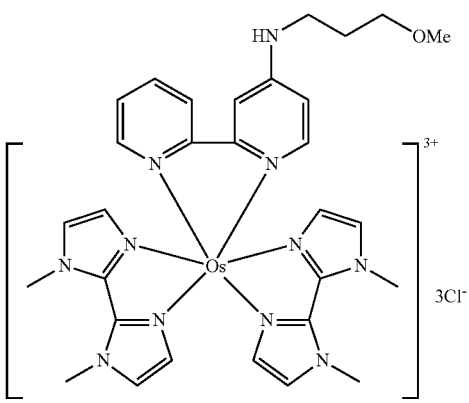 [Os(1,1'-dimethyl-2,2'-biimidazole)$_2$(4-(3-methoxypropyl)amino-2,2'-bipyridine)]Cl$_3$ | −97 |
| VI | 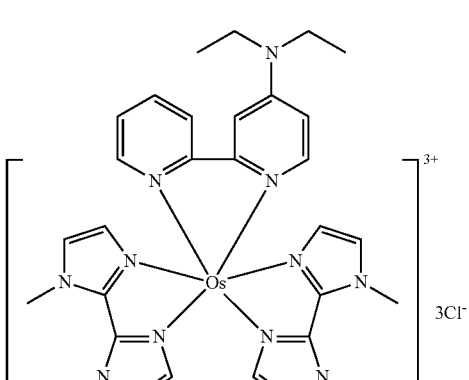 [Os(1,1'-dimethyl-2,2'-biimidazole)$_2$(4-diethylamino-2,2'-bipyridine)]Cl$_3$ | −120 |

TABLE 1-continued

Redox Potentials of Selected Transition Metal Complexes

| Complex | Structure | $E_{1/2}$(vs Ag/AgCl)/mV* |
|---|---|---|
| VII | [Os(1,1'-dimethyl-2,2'-biimidazole)$_2$(4,4'-dimethyl-2,2'-bipyridine)]Cl$_3$ | 32 |
| VIII | [Os(1,1'-dimethyl-2,2'-biimidazole)$_2$(4-(6-hydroxyhexyl)amino-2,2'-bipyridine)]Cl$_3$ | −100 |
| IX | [Os(1,1'-dimethyl-2,2'-biimidazole)$_2$(4-(6-aminohexyl)amino-2,2'-bipyridine)]Cl$_3$ | −93 |

TABLE 1-continued

Redox Potentials of Selected Transition Metal Complexes

| Complex | Structure | $E_{1/2}$(vs Ag/AgCl)/mV* |
|---|---|---|
| X | [Os(1,1'-dimethyl-2,2'-biimidazole)$_2$(4-methoxypyridine)$_2$]Cl$_3$ | −125 |
| XI | [Os(1,1'-dimethyl-2,2'-biimidazole)$_2$(4-(N-(4-carboxy)piperidino)-2,2'-bipyridine)]Cl$_3$ | −60 |
| XII | [Os(1,1'-dimethyl-2,2'-biimidazole)$_2$(1-methyl-2-(2-pyridyl)imidazole)]Cl$_3$ | −74 |

TABLE 1-continued

Redox Potentials of Selected Transition Metal Complexes

| Complex | Structure | $E_{1/2}$(vs Ag/AgCl)/mV* |
|---|---|---|
| XIII | 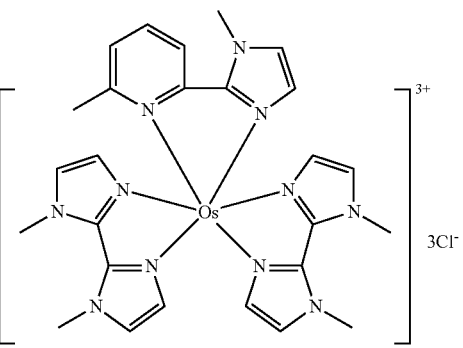 [Os(1,1'-dimethyl-2,2'-biimidazole)$_2$(1-methyl-2-(6-methylpyrid-2-yl)imidazole)]Cl$_3$ | −97 |
| IVX | 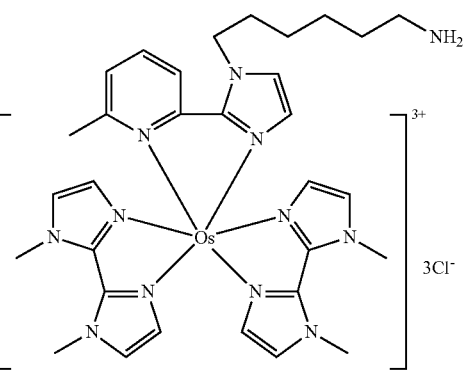 [Os(1,1'-dimethyl-2,2'-biimidazole)$_2$(1-(6-aminohexyl)-2-(6-methylpyrid-2-yl)imidazole)]Cl$_3$ | −81 |
| VX | 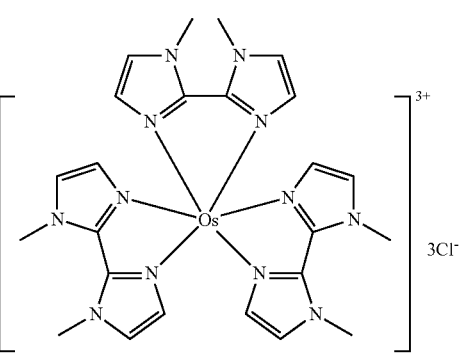 [Os(3,3'-dimethyl-2,2'-biimidazole)$_3$]Cl$_3$ | −230 |

*Redox potentials were estimated by averaging the positions of the reduction wave peaks and the oxidation wave peaks of cyclic voltammograms (CVs) obtained in pH 7 PBS buffer with a glassy carbon working electrode, a graphite counter electrode and a standard Ag/AgCl reference electrode at a sweep rate of 50 mV/s.

The transition metal complexes of Formula 1 also include transition metal complexes that are coupled to a polymeric backbone through one or more of L, $L_1$, $L_2$, $L_3$, and $L_4$. Additional examples of suitable transition metal complexes are described in U.S. patent application Ser. No. 09/712,065, now U.S. Pat. No. 6,605,200, entitled "Polymeric Transition Metal Complexes and Uses Thereof", filed on even date herewith, incorporated herein by reference. In some embodiments, the polymeric backbone has functional groups that act as ligands of the transitional metal complex. Such polymeric backbones include, for example, poly(4-vinylpyridine) and poly(N-vinylimidazole) in which the pyridine and imidazole groups, respectively, can act as monodentate ligands of the transition metal complex. In other embodiments, the transition metal complex can be the reaction product between a reactive group on a precursor polymer and a reactive group on a ligand of a precursor transition metal complex (such as a complex of Formula 1 where one of L, $L_1$, $L_2$, $L_3$ and $L_4$ includes a reactive group as described above). Suitable precursor polymers include, for example, poly(acrylic acid)

(Formula 11), styrene/maleic anhydride copolymer (Formula 12), methylvinylether/maleic anhydride copolymer (GAN-TREX polymer) (Formula 13), poly(vinylbenzylchloride) (Formula 14), poly(allylamine) (Formula 15), polylysine (Formula 16), carboxy-poly(vinylpyridine (Formula 17), and poly(sodium 4-styrene sulfonate) (Formula 18).

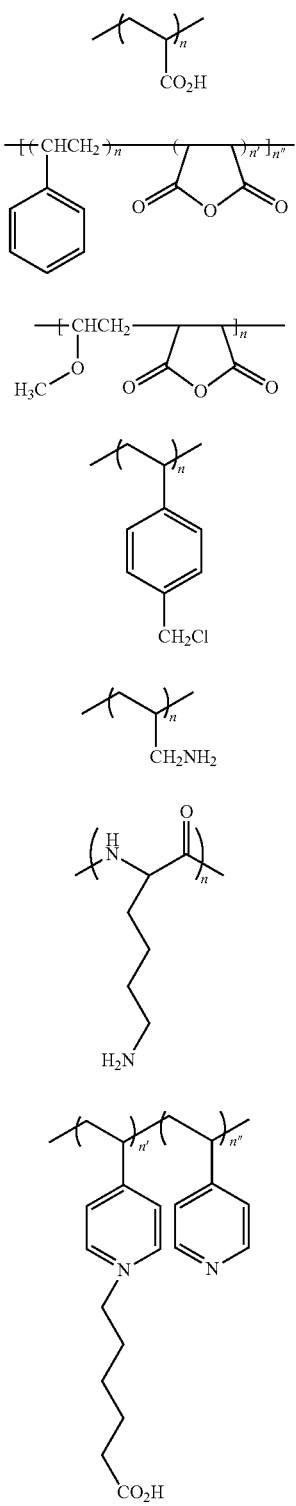

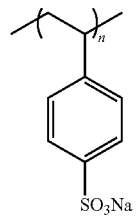

The spacer couples the transition metal complex to the polymeric backbone. In some embodiments, the spacer includes at least one non-cyclic functional group selected from the group consisting of —(CR'R$^s$)—, —O—, —S—, —C(O)O—, —S(O)$_2$NR$^k$—, —OC(O)NR$^m$—, —OC(S)NR$^n$—, —C(O)NR$^t$—, —NR$^u$—, —CR$^v$=N—O—, —CR$^w$=NNR$^x$—, and —(SiR$^y$R$^z$)—, where R$^r$ and R$^s$ are independently hydrogen, chlorine, fluorine, or substituted or unsubstituted alkyl, alkoxy, alkenyl, or alkynyl and R$^k$, R$^m$, R$^n$, R$^t$, R$^u$, R$^v$, R$^w$, R$^x$, R$^y$, and R$^z$ are independently hydrogen or substituted or unsubstituted alkyl. Preferably, the spacer includes at least four, and, more preferably, at least eight of these non-cyclic functional groups. Preferably, the non-cyclic functional group(s) is/are selected from the group consisting of —(CR'R$^s$)—, —O—, —S—, —C(O)O—, —S(O)$_2$NR$^k$—, —OC(O)NR$^m$—, —OC(S)NR$^n$—, —C(O)NR$^t$—, —NR$^u$—, —CR$^v$=N—O—, —CR$^w$=NNR$^x$—, and —(SiR$^y$R$^z$)—, where R$^k$, R$^m$, R$^n$, R$^t$, R$^u$, R$^v$, R$^w$, R$^x$, R$^y$, and R$^z$ are independently selected from the group consisting of hydrogen and substituted or unsubstituted alkyl. In one embodiment, the preferred spacer includes a 4 to 30 atom long linear segment, the linear segment having any combination of the following bonds to form the 4 to 30 atom chain of the segment: C—C, C—N, C—O, C—Si, C—S, S—N, and Si—O.

Alternatively, the transition metal complex can have reactive group(s) for immobilization or conjugation of the complexes to other substrates or carriers, examples of which include, but are not limited to, macromolecules (e.g., enzymes) and surfaces (e.g., electrode surfaces).

For reactive attachment to polymers, substrates, or other carriers, the transition metal complex precursor includes at least one reactive group that reacts with a reactive group on the polymer, substrate, or carrier. Typically, covalent bonds are formed between the two reactive groups to generate a linkage. Examples of such linkages are provided in Table 2, below. Generally, one of the reactive groups is an electrophile and the other reactive group is a nucleophile.

TABLE 2

Examples of Reactive Group Linkages

| First Reactive Group | Second Reactive Group | Resulting Linkage |
|---|---|---|
| Activated ester* | Amine | Carboxamide |
| Acrylamide | Thiol | Thioether |
| Acyl azide | Amine | Carboxamide |
| Acyl halide | Amine | Carboxamide |
| Carboxylic acid | Amine | Carboxamide |
| Aldehyde or ketone | Hydrazine | Hydrazone |
| Aldehyde or ketone | Hydroxyamine | Oxime |
| Alkyl halide | Amine | Alkylamine |
| Alkyl halide | Carboxylic acid | Carboxylic ester |
| Alkyl halide | Imidazole | Imidazolium |
| Alkyl halide | Pyridine | Pyridinium |
| Alkyl halide | Alcohol/phenol | Ether |
| Alkyl halide | Thiol | Thioether |

TABLE 2-continued

Examples of Reactive Group Linkages

| First Reactive Group | Second Reactive Group | Resulting Linkage |
|---|---|---|
| Alkyl sulfonate | Thiol | Thioether |
| Alkyl sulfonate | Pyridine | Pyridinium |
| Alkyl sulfonate | Imidazole | Imidazolium |
| Alkyl sulfonate | Alcohol/phenol | Ether |
| Anhydride | Alcohol/phenol | Ester |
| Anhydride | Amine | Carboxamide |
| Aziridine | Thiol | Thioether |
| Aziridine | Amine | Alkylamine |
| Aziridine | Pyridine | Pyridinium |
| Epoxide | Thiol | Thioether |
| Epoxide | Amine | Alkylamine |
| Epoxide | Pyridine | Pyridinium |
| Halotriazine | Amine | Aminotriazine |
| Halotriazine | Alcohol | Triazinyl ether |
| Imido ester | Amine | Amidine |
| Isocyanate | Amine | Urea |
| Isocyanate | Alcohol | Urethane |
| Isothiocyanate | Amine | Thiourea |
| Maleimide | Thiol | Thioether |
| Sulfonyl halide | Amine | Sulfonamide |

*Activated esters, as understood in the art, generally include esters of succinimidyl, benzotriazolyl, or aryl substituted by electron-withdrawing groups such as sulfo, nitro, cyano, or halo; or carboxylic acids activated by carbodiimides.

In some embodiments, the spacer includes a flexible linear chain of at least four atoms. Preferably, the flexible linear chain includes at least six or eight atoms, but less than about 30 atoms. More preferably, the number of atoms forming the flexible linear chain ranges from 8 to 18. In some instances, two or more flexible chains are included in the spacer. The flexible chain typically permits the spacer to move relative to the polymeric backbone, thereby allowing the transition metal complex on the end of the spacer to move. This is particularly useful for polymeric transition metal complexes that are used as redox mediators because the movement of the transition metal complex coupled by the spacer to the polymer backbone can facilitate transfer of electrons between transition metal complexes and with the electrode. This can enhance the electron transfer rate and can facilitate the desired electrochemical reaction at the electrode by, for example, improving the conduction lo of electrons by the crosslinked and hydrated polymer on the electrode.

In addition to the chains, the spacer can contain one or more other unsaturated groups. For example, the spacer can include an unsaturated functional group such as those listed in Table 1 under the heading "Resulting Linkage". As another example, the spacer can include a heterocycle or aryl group. For example, the spacer group of poly(4-vinylpyridine) or poly(N-vinylimidazole) would include a pyridine or imidazole functional group. In these specific instances, the heterocycle or aryl group is positioned between the flexible chain and the polymeric backbone, although this is not necessary to the invention.

Formula 17 schematically represent examples of the polymeric transition metal complexes of the present invention.

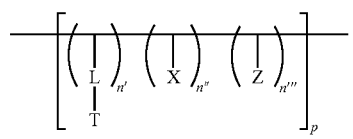

17

In general, the polymeric transition metal complex has a polymeric backbone with one or more types of pendant groups (represented in Formula 17 as L-T, X, and Z, respectively). The individual pendant groups, L-T, X, and Z, of each polymer unit can be ordered in any configuration. The number of polymer units is represent by p, which is an integer having a value of one or more. The product of p and $(n'+n''+n''')$ is generally at least 5, preferably, at least 10, and can be 50 or more.

T is a transition metal complex as described above. L is a spacer group, as described above, and couples the transition metal complex, T, to the polymeric backbone. The number of spacer group-transition metal complex units (L-T) attached to the polymer backbone in each polymer unit is represented by n', which is an integer having a value of one or more.

X represents a pendant groups that does not contain a reactive substituent. The number of these pendant groups attached to the polymer backbone in each polymer unit is represented by n'', which is an integer having a value of zero or more.

Z represents a pendant group substituted with a reactive substituent that includes, but is not limited to, pyridyl, imidazolyl, carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. The pendant group, Z, can be used for cross-linking the polymer backbone during, for example, polymer immobilization on a surface. The number of these pendant groups attached to the polymer backbone in each polymer unit is represented by n''', which is an integer having a value of zero or more.

The polymeric transition metal complex typically has a weight average molecular weight of at least 5000, although in some instances lower molecular weight polymeric transition metal complexes can be used. The weight average molecular weight of the polymeric transition metal complex can be at least 10,000, 50,000, 100,000, or more and can depend on the application. This weight average molecular weight generally refers to the weight average molecular weight prior to crosslinking to form a film.

An example of a precursor polymer that can be used to form a polymeric transition metal complex is presented as Formula 18. This precursor polymer is poly(4-vinylpyridine) quaternized with an alkyl moiety substituted with a reactive group.

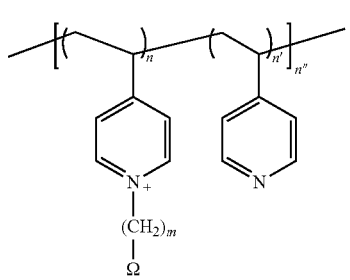

18 where Ω is the reactive group, m is typically 1 to 18, n and n' are the average numbers of pyridinium and pyridine subunits respectively in each repeating polymer unit, and n'' is the number of repeating polymer units.

Examples of polymeric transition metal complexes formed using this precursor polymer are illustrated by Formulas 19, 20 and 21:

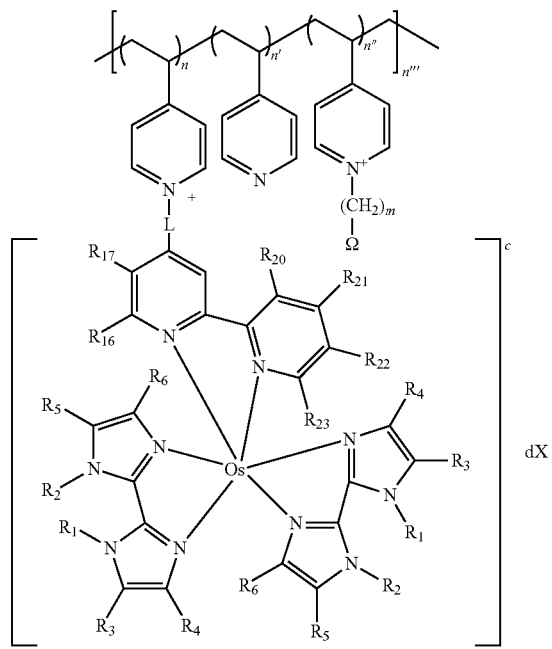

19

-continued

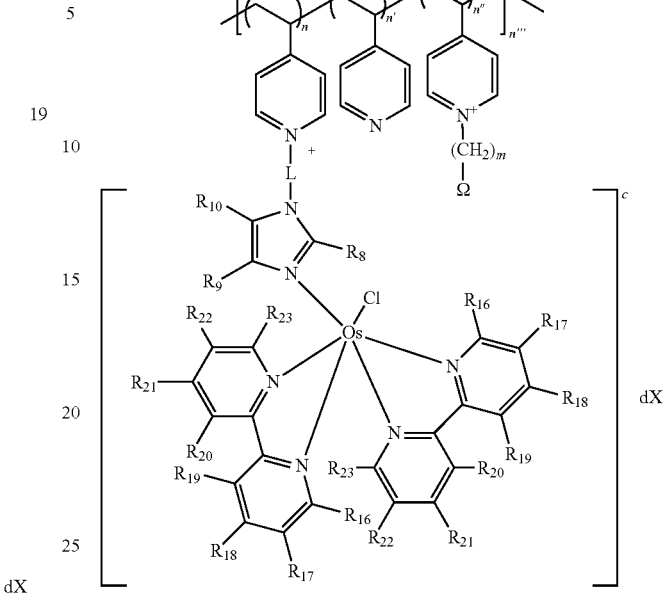

21 where Ω is the reactive group; m is 1 to 18; L is the spacer, as described above, formed by the reaction of the transition metal complex to the Ω; X represents counter ions; d represents the number of counter ions; c is an integer representing the charge of the complex; and $R_1$, $R_2$, $R_3$, $R_3$, $R_4$, $R_5$, $R_6$, $R_8$, $R_9$, $R_{10}$, $R_{16}$, $R_{17}$, $R_{18}$, $R_{19}$, $R_{20}$, $R_{21}$, $R_{22}$, $R_{23}$, $R'_3$, $R'_4$, $R_a$, $R_b$, $R_c$, and $R_d$ are as described above.

Specific examples of suitable polymeric transition metal complexes are illustrated in Formulas 22, 23, and 24.

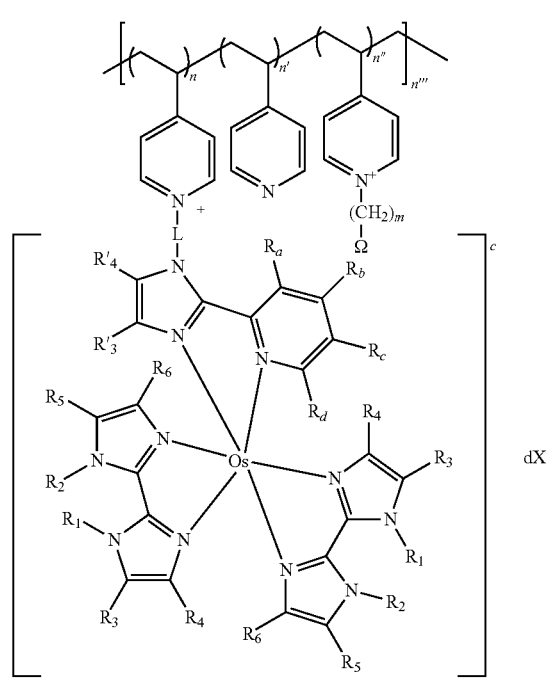

20

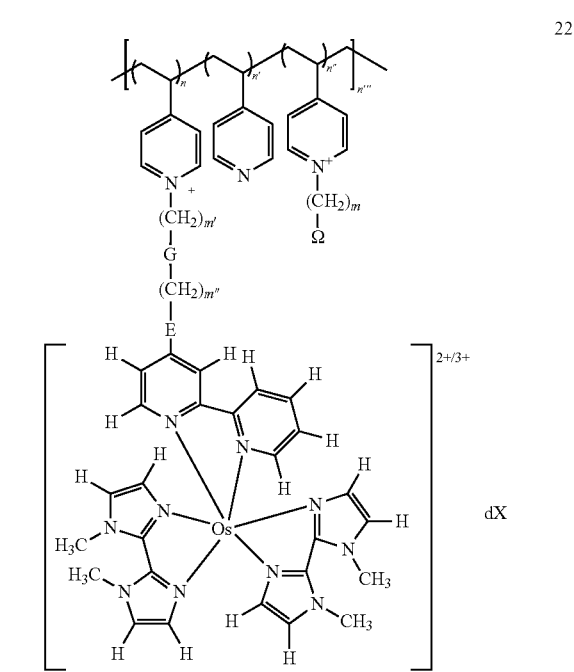

22

-continued

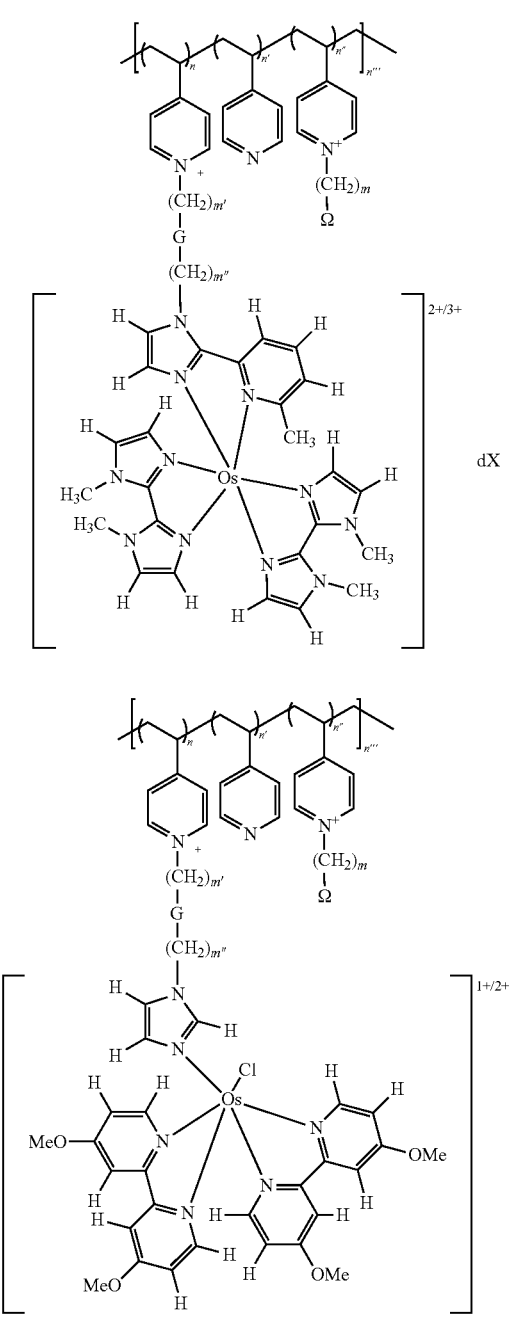

where G represents one of the "Resulting Linkages" of Table 1 such as, for example, an amide having the formula: —CONR$_{30}$— or —NR$_{30}$CO—, where R$_{30}$ is a hydrogen, methyl, ethyl or other 1 to 6 carbon alkyl. E is O, S or NR$_{31}$, where R$_{31}$ is hydrogen, methyl, ethyl or other 1 to 6 carbon alkyl. m' and m are the same and are typically in the range of 1 to 18 and m" is independently in the range of 1 to 18.

Transition metal complexes of the present invention can be soluble in water or other aqueous solutions, or in organic solvents. In general, the transition metal complexes can be made soluble in either aqueous or organic solvents by having an appropriate counter ion or ions, X. For example, transition metal complexes with small counter anions, such as F$^-$, Cl$^-$, and Br$^-$, tend to be water soluble. On the other hand, transition metal complexes with bulky counter anions, such as I$^-$, BF$_4^-$ and PF$_6^-$, tend to be soluble in organic solvents. Preferably, the solubility of transition metal complexes of the present invention is greater than about 0.1 M (moles/liter) at 25° C. for a desired solvent.

The transition metal complexes discussed above are useful as redox mediators in electrochemical sensors for the detection of analytes in bio-fluids. The use of transition metal complexes as redox mediators is described, for example, in U.S. Pat Nos. 5,262,035; 5,262,305; 5,320,725; 5,356,786; 5,593,852; 5,665,222; 5,972,199; and 6,143,164 and U.S. patent applications Ser. Nos. 09/034,372, (now U.S. Pat. No. 6,134,461); 09/070,677, (now U.S. Pat. No. 6,175,752); 09/295,962, (now U.S. Pat. No. 6,338,790) and 09/434,026, all of which are herein incorporated by reference. The transitional metal complexes described herein can typically be used in place of those discussed in the references listed above. The transitions metal complexes that include a polymeric backbone and are redox mediators can also be referred to as "redox polymers".

In general, the redox mediator is disposed on or in proximity to (e.g., in a solution surrounding) a working electrode. The redox mediator transfers electrons between the working electrode and an analyte. In some preferred embodiments, an enzyme is also included to facilitate the transfer. For example, the redox mediator transfers electrons between the working electrode and glucose (typically via an enzyme) in an enzyme-catalyzed reaction of glucose. Redox polymers are particularly useful for forming non-leachable coatings on the working electrode. These can be formed, for example, by crosslinking the redox polymer on the working electrode, or by crosslinking the redox polymer and the enzyme on the working electrode Transition metal complexes can enable accurate, reproducible and quick or continuous assays. Transition metal complex redox mediators accept electrons from, or transfer electrons to, enzymes or analytes at a high rate and also exchange electrons rapidly with an electrode. Typically, the rate of self exchange, the process in which a reduced redox mediator transfers an electron to an oxidized redox mediator, is rapid. At a defined redox mediator concentration, this provides for more rapid transport of electrons between the enzyme (or analyte) and electrode, and thereby shortens the response time of the sensor. Additionally, the novel transition metal complex redox mediators are typically stable under ambient light and at the temperatures encountered in use, storage and transportation. Preferably, the transition metal complex redox mediators do not undergo chemical change, other than oxidation and reduction, in the period of use or under the conditions of storage, though the redox mediators can be designed to be activated by reacting, for example, with water or the analyte.

The transition metal complex can be used as a redox mediator in combination with a redox enzyme to electrooxidize or electroreduce the analyte or a compound derived of the analyte, for example by hydrolysis of the analyte. The redox potentials of the redox mediators are generally more positive (i.e. more oxidizing) than the redox potentials of the redox enzymes when the analyte is electrooxidized and more negative when the analyte is electroreduced. For example, the redox potentials of the preferred transition metal complex redox mediators used for electrooxidizing glucose with glucose oxidase or PQQ-glucose dehydrogenase as enzyme is between about −200 mV and +200 mV versus a Ag/AgCl reference electrode, and the most preferred mediators have redox potentials between about −100 mV and about +100 mV versus a Ag/AgCl reference electrode

Crosslinking in Transition Metal Complex Polymers

Electron transport involves an exchange of electrons between segments of the redox polymers (e.g., one or more transition metal complexes coupled to a polymeric backbone, as described above) in a crosslinked film disposed on an electrode. The transition metal complex can be bound to the polymer backbone though covalent, coordinative or ionic bonds, where covalent and coordinative binding are preferred. Electron exchange occurs, for example, through the collision of different segments of the crosslinked redox polymer. Electrons transported through the redox polymer can originate from, for example, electrooxidation or electroreduction of an enzymatic substrate, such as, for example, the oxidation of glucose by glucose oxidase.

The degree of crosslinking of the redox polymer can influence the transport of electrons or ions and thereby the rates of the electrochemical reactions. Excessive crosslinking of the polymer can reduce the mobility of the segments of the redox polymer. A reduction in segment mobility can slow the diffusion of electrons or ions through the redox polymer film. A reduction in the diffusivity of electrons, for example, can require a concomitant reduction in the thickness of the film on the electrode where electrons or electron vacancies are collected or delivered. The degree of crosslinking in a redox polymer film can thus affect the transport of electrons from, for example, an enzyme to the transition metal redox centers of the redox polymer such as, for example, $Os^{2+/3+}$ metal redox centers; between redox centers of the redox polymer; and from these transition metal redox centers to the electrode.

Inadequate crosslinking of a redox polymer can result in excessive swelling of the redox polymer film and to the leaching of the components of the redox polymer film. Excessive swelling can also result in the migration of the swollen polymer into the analyzed solution, in the softening of the redox polymer film, in the film's susceptibility to removal by shear, or any combination of these effects.

Crosslinking can decrease the leaching of film components and can improve the mechanical stability of the film under shear stress. For example, as disclosed in Binyamin, G. and Heller, A; *Stabilization of Wired Glucose Oxidase Anodes Rotating at* 1000 rpm at 37° C.; Journal of the Electrochemical Society, 146 (8), 2965-2967, 1999, herein incorporated by reference, replacing a difunctional crosslinker, such as polyethylene glycol diglycidyl ether, with a trifunctional crosslinker such as N,N -diglycidyl-4-glycidyloxyaniline, for example, can reduce leaching and shear problems associated with inadequate crosslinking.

Examples of other bifunctional, trifunctional and tetrafunctional crosslinkers are listed below:

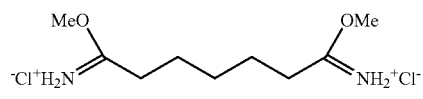

Amine-reactive Bifunctional Crosslinkers

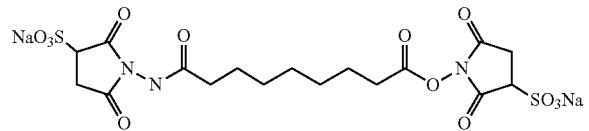

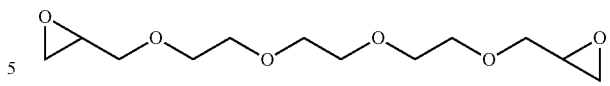

Pyridine- or Imidazole-reactive Bifunctional Crosslinkers

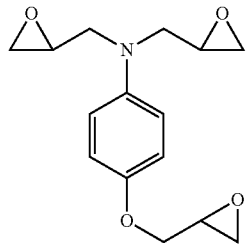

Pyridine- or Imidazole-reactive trifunctional Crosslinker

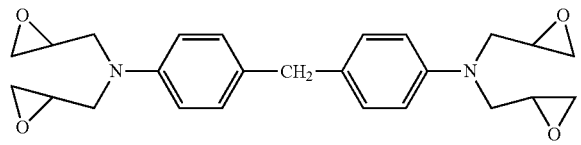

Pyridine- or Imidazole-reactive Tetrafunctional Crosslinkers

Alternatively, the number of crosslinking sites can be increased by reducing the number of transition metal complexes attached to the polymeric backbone, thus making more polymer pendant groups available for crosslinking. One important advantage of at least some of the redox polymers is the increased mobility of the pendant transition metal complexes, resulting from the flexibility of the pendant groups. As a result, in at least some embodiments, fewer transition metal complexes per polymer backbone are needed to achieve a desired level of diffusivity of electrons and current density of analyte electrooxidation or electroreduction.

Coordination in Transition Metal Complex Polymers

Transition metal complexes can be directly or indirectly attached to a polymeric backbone, depending on the availability and nature of the reactive groups on the complex and the polymeric backbone. For example, the pyridine groups in poly(4-vinylpyridine) or the imidazole groups in poly(N-vinylimidazole) are capable of acting as monodentate ligands and thus can be attached to a metal center directly. Alternatively, the pyridine groups in poly(4-vinylpyridine) or the imidazole groups in poly(N-vinylimidazole) can be quaternized with a substituted alkyl moiety having a suitable reactive group, such as a carboxylate function, that can be activated to form a covalent bond with a reactive group, such as an amine, of the transition metal complex. (See Table 2 for a list of other examples of reactive groups.)

Redox centers such as, for example, $Os^{2+/3+}$ can be coordinated with five heterocyclic nitrogens and an additional ligand such as, for example, a chloride anion. An example of such a coordination complex includes two bipyridine ligands which form stable coordinative bonds, the pyridine of poly (4-vinylpyridine) which forms a weaker coordinative bond, and a chloride anion which forms the least stable coordinative bond.

Alternatively, redox centers, such as $Os^{2+/3+}$, can be coordinated with six heterocyclic nitrogen atoms in its inner coordination sphere. The six coordinating atoms are preferably paired in the ligands, for example, each ligand is composed of at least two rings. Pairing of the coordinating atoms can influence the potential of an electrode used in conjunction with redox polymers of the present invention.

Typically, for analysis of glucose, the potential at which the working electrode, coated with the redox polymer, is poised is negative of about +250 mV vs. SCE (standard calomel electrode). Preferably, the electrode is poised negative of about +150 mV vs. SCE. Poising the electrode at these potentials reduces the interfering electrooxidation of constituents of biological solutions such as, for example, urate, ascorbate and acetaminophen. The potential can be modified by altering the ligand structure of the complex.

The redox potential of a redox polymer, as described herein, is related to the potential at which the electrode is poised. Selection of a redox polymer with a desired redox potential allows tuning of the potential at which the electrode is best poised. The redox potentials of a number of the redox polymers described herein are negative of about +150 mV vs. SCE and can be negative of about +50 mV vs. SCE to allow the poising of the electrode potentials negative of about +250 mV vs. SCE and preferably negative of about +150 mV vs. SCE.

The strength of the coordination bond can influence the potential of the redox centers in the redox polymers. Typically, the stronger the coordinative bond, the more positive the redox potential. A shift in the potential of a redox center resulting from a change in the coordination sphere of the transition metal can produce a labile transition metal complex. For example, when the redox potential of an $Os^{2+/3+}$ complex is downshifted by changing the coordination sphere, the complex becomes labile. Such a labile transition metal complex may be undesirable when fashioning a metal complex polymer for use as a redox mediator and can be avoided through the use of weakly coordinating multidentate or chelating heterocyclics as ligands.

Electrode Interference

Transition metal complexes used as redox mediators in electrodes can be affected by the presence of transition metals in the analyzed sample including, for example, $Fe^{3+}$ or $Zn^{2+}$. The addition of a transition metal cation to a buffer used to test an electrode results in a decline in the current produced. The degree of current decline depends on the presence of anions in the buffer which precipitate the transition metal cations. The lesser the residual concentration of transition metal cations in the sample solution, the more stable the current. Anions which aid in the precipitation of transition metal cations include, for example, phosphate. It has been found that a decline in current upon the addition of transition metal cations is most pronounced in non-phosphate buffers. If an electrode is transferred from a buffer containing a transition metal cation to a buffer substantially free of the transition metal cation, the original current is restored.

The decline in current is thought to be due to additional crosslinking of a pyridine-containing polymer backbone produced by the transition metal cations. The transition metal cations can coordinate nitrogen atoms of different chains and chain segments of the polymers. Coordinative crosslinking of nitrogen atoms of different chain segments by transition metal cations can reduce the diffusivity of electrons.

Serum and other physiological fluids contain traces of transition metal ions, which can diffuse into the films of electrodes made with the redox polymers of the present invention, lowering the diffusivity of electrons and thereby the highest current reached at high analyte concentration. In addition, transition metal ions like iron and copper can bind to proteins of enzymes and to the reaction centers or channels of enzymes, reducing their turnover rate. The resulting decrease in sensitivity can be remedied through the use of anions which complex with interfering transition metal ions, for example, in a buffer employed during the production of the transition metal complex. A non-cyclic polyphosphate such as, for example, pyrophosphate or triphosphate, can be used. For example, sodium or potassium non-cyclic polyphosphate buffers can be used to exchange phosphate anions for those anions in the transition metal complex which do not precipitate transition metal ions. The use of linear phosphates can alleviate the decrease in sensitivity by forming strong complexes with the damaging transition metal ions, assuring that their activity will be low. Other complexing agents can also be used as long as they are not electrooxidized or electroreduced at the potential at which the electrode is poised.

Enzyme Damage and its Alleviation

Glucose oxidase is a flavoprotein enzyme that catalyzes the oxidation by dioxygen of D-glucose to D-glucono-1,5-lactone and hydrogen peroxide. Reduced transition metal cations such as, for example, $Fe^{2+}$, and some transition metal complexes, can react with hydrogen peroxide. These reactions form destructive OH radicals and the corresponding oxidized cations. The presence of these newly formed transition metal cations can inhibit the enzyme and react with the metal complex. Also, the oxidized transition metal cation can be reduced by the $FADH_2$ centers of an enzyme, or by the transition metal complex.

Inhibition of the active site of an enzyme or a transition metal complex by a transition metal cation, as well as damaging reactions with OH radicals can be alleviated, thus increasing the sensitivity and functionality of the electrodes by incorporating non-cyclic polyphosphates, as discussed above. Because the polyphosphate/metal cation complex typically has a high (oxidizing) redox potential, its rate of oxidation by hydrogen peroxide is usually slow. Alternatively, an enzyme such as, for example, catalase, can be employed to degrade hydrogen peroxide.

EXAMPLES

Unless indicated otherwise, all of the chemical reagents are available from Aldrich Chemical Co. (Milwaukee, Wis.) or other sources. Additional examples are provided in U.S. Pat. No. 6,605,200 entitled "Polymeric Transition Metal Complexes and Uses Thereof", incorporated herein by reference. For purposes of illustration, the synthesis of several transition metal complex ligands are shown below:

Example 1

Synthesis of
4-(5-carboxypentyl)amino-2,2'-bipyridyl

This example illustrates how a carboxy reactive group is introduced onto a 2,2'-bipyridyl derivative.

Synthesis of compound D: To compound C (formed from A and B according to

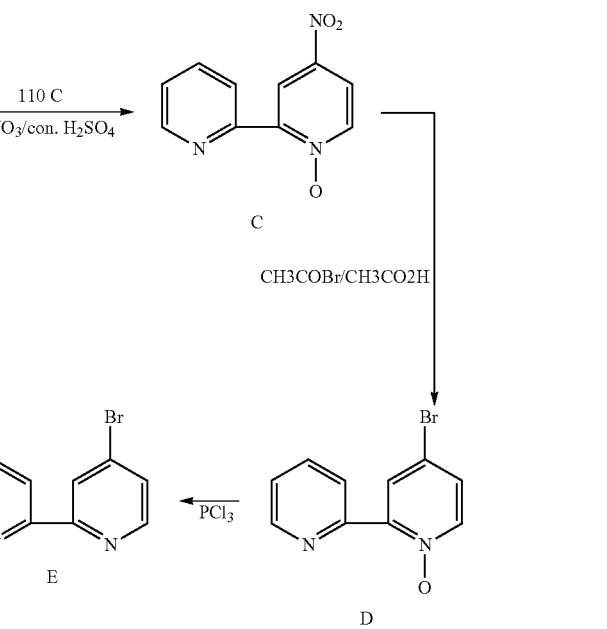
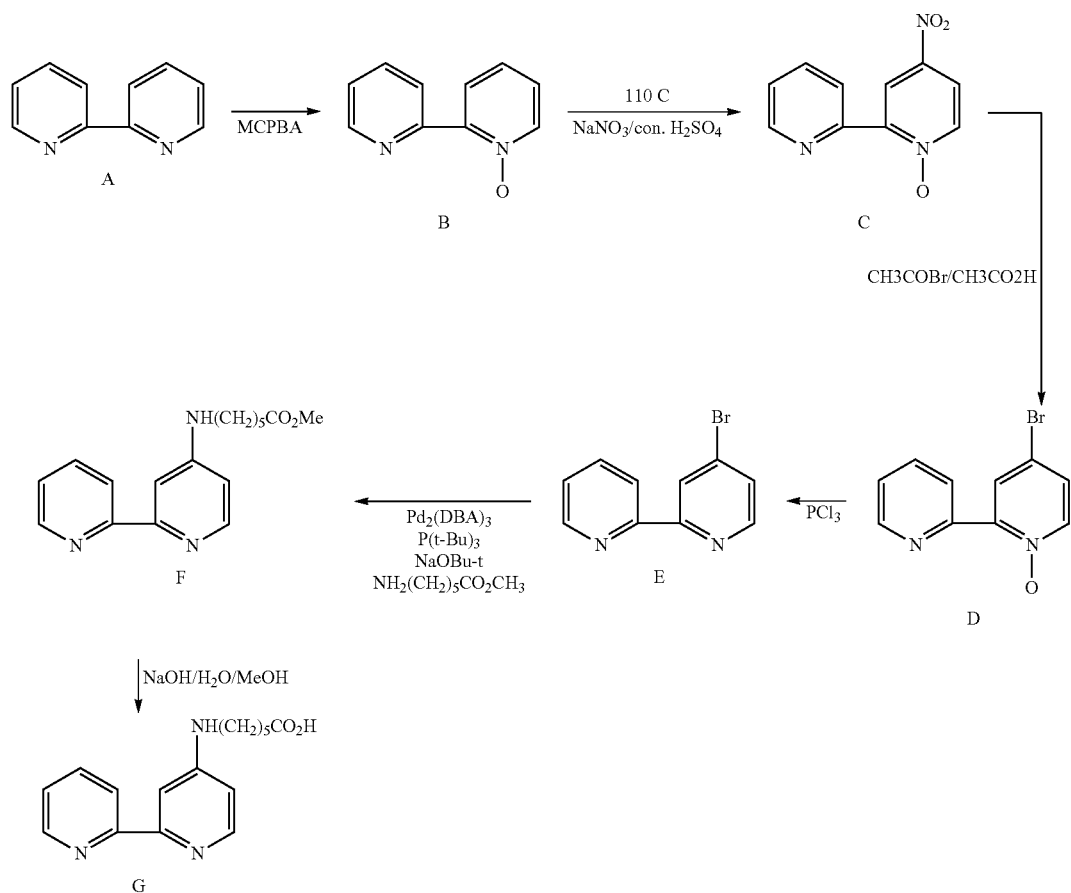

Wenkert, D.; Woodward, R. B. *J. Org. chem.* 48, 283 (1983)) (5 g) dissolved in 30 mL acetic acid in a 100 ml round bottom flask was added 16 mL acetyl bromide. The yellow mixture was refluxed for 1.5 h and then rotovaporated to dryness. The resulting light yellow solid of D was sufficiently pure enough for the next step without further purification. Yield: 95%

Synthesis of compound E: To a stirred suspension of compound D in 60 mL CHCl$_3$ was added 12 mL PCl$_3$ at room temperature. The mixture was refluxed for 2 h under N$_2$ and then cooled to room temperature. The reaction mixture was poured into 100 mL ice/water. The aqueous layer was separated and saved. The CHCl$_3$ layer was extracted three times with H$_2$O (3×60 mL) and then discarded. The combined aqueous solution was neutralized with NaHCO$_3$ powder to about pH 7 to 8. The resulting white precipitate was collected by suction filtration, washed with H$_2$O (30 mL) and then dried under vacuum at 50° C. for 24 h. Yield: 85%.

Synthesis of compound F: Compound F was synthesized from compound E (5 g) and 6-aminocaproic acid methyl ester (6 g) using the palladium-catalyzed amination method of aryl bromides described by Hartwig et al. (Hartwig, J. F., et al. *J. Org. Chem.* 64, 5575 (1999)). Yield: 90%.

Synthesis of compound G: Compound F (3 g) dissolved in 20 mL MeOH was added to a solution of NaOH (0.6 g) in 30 mL H$_2$O. The resulting solution was stirred at room temperature for 24 h and then neutralized to pH 7 with dilute HCl. The solution was saturated with NaCl and then extracted with CHCl$_3$. The CHCl$_3$ extract was evaporated to dryness and then purified by a silica gel column eluted with 10% H$_2$O/CH$_3$CN. Yield: 70%.

Example 2

Synthesis of a 4-(((6-Aminohexyl)amino)-2,2'-bipyridine

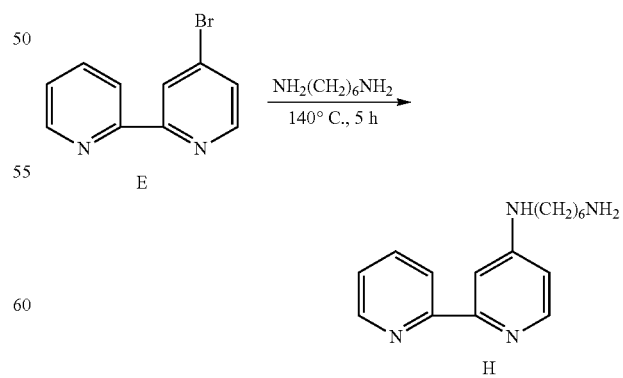

This example illustrates the general synthesis of a 2,2'-bipyridyl with an amine reactive group.

Synthesis of compound H: A mixture of compound E (2.5 g) and 1,6-diaminohexane (15 g) in a 250 mL round bottom flask was heated under N$_2$ at 140° C. in an oil bath for 4-5 h. Excess 1,6-diaminohexane was removed by high vacuum distillation at 90-120° C. The product was purified by a silica gel column, eluting with 5% NH$_4$OH in isopropyl alcohol. Yield: 70%.

Example 3

Synthesis of 1,1'-dimethyl-2,2'-biimidazole

This example illustrates the synthesis of 2,2'-biimidazole derivatives.

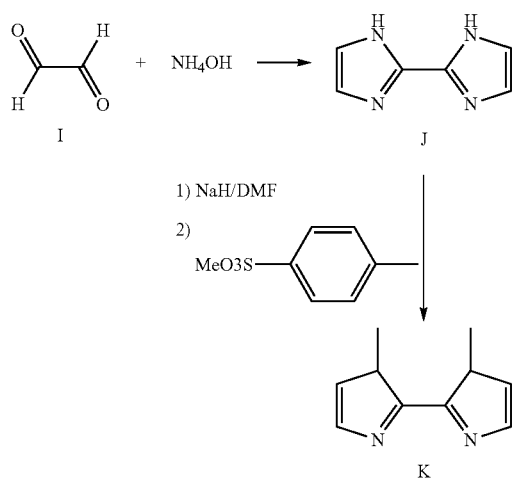

The alkylation step can be carried out stepwise so two different alkyl groups can be introduced. For example:

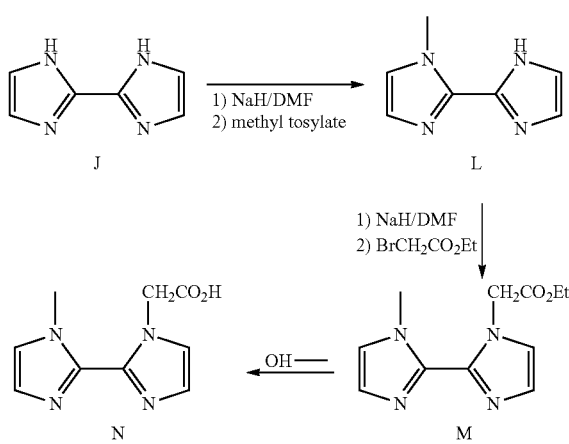

Synthesis of compound K: To a stirred solution of compound J (formed from 1 according to Fieselmann, B. F., et al. *Inorg. Chem.* 17, 2078 (1978)) (4.6 g, 34.3 mmoles) in 100 mL dry DMF in a 250 ml round bottom flask cooled in an ice/water bath was added in portions NaH (60% in mineral oil, 2.7 g, 68.6 mmoles). After the solution was stirred at 0° C. for one more hour under N$_2$, methyl toluenesulfonate (10.3 mL, 68.6 mmoles) was added in small portions using a syringe over 30 min. The stirring of the solution in the ice/water bath was continued for 1 h and then at room temperature for 3 h. The solvent was removed by vacuum distillation. The dark residue was triturated with ether and then suction filtered and dried under vacuum. The product was purified by sublimation. Yield: 80%.

Synthesis of compound L: Compound L was prepared using the method described for the synthesis of compound K except that only one equivalent each of compound J, NaH and methyl toluenesulfonate was used. The product was purified by sublimation.

Synthesis of compound M: To a stirred solution of compound L (1 g, 6.8 mmoles) in 20 mL dry DMF in a 50 ml round bottom flask cooled in a ice/water bath is added in portions NaH (60% in mineral oil, 0.27 g, 6.8 mmoles). After the solution is stirred at 0° C. for one more hour under N$_2$, ethyl bromoacetate (0.75 mL, 6.8 mmoles) is added in small portions via a syringe over 15 min. The stifling of the solution is continued in the ice/water bath for 1 h and then at room temperature for 3 h. The solvent is removed by vacuum distillation. The product is purified by a silica gel column using 10% MeOH/CHCl$_3$ as the eluent.

Synthesis of Compound N: Compound M (1 g) is hydrolyzed using the method described for the synthesis of compound G. The product is purified by a silica gel column using 10% H$_2$O/CH$_3$CN as the eluent.

Example 4

Synthesis of 2-(2-Pyridyl)imidazole Heterobidentate Ligands

This example illustrates a general synthesis of heterobidentate ligands containing an imidazole ring.

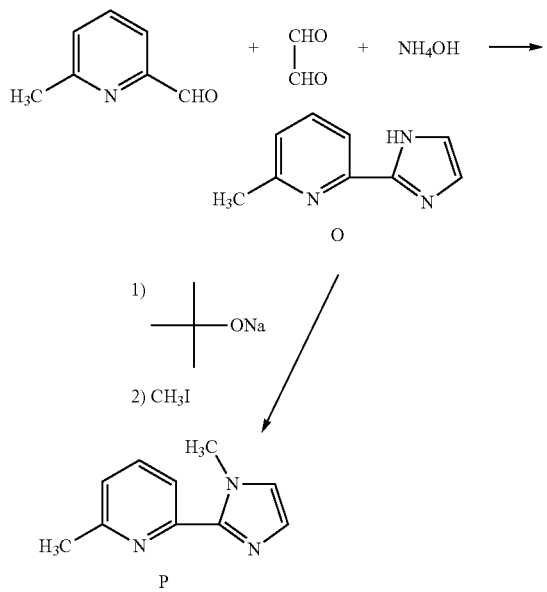

Synthesis of compound O: A solution of 6-methylpyridine-2-carboxaldehyde (26 g, 0.21 mole) and glyoxal (40%, 30 mL) in 50 mL EtOH in a three-necked 250 mL round bottom flask fitted with a thermometer and an addition funnel was stirred in a NaCl/ice bath. When the solution was cooled to below 5° C., conc. NH$_4$OH was added dropwise through the addition funnel. The rate of the addition was controlled so that the temperature of the solution was maintained at below 5° C. After the addition, the stifling of the yellow solution was continued in the ice bath for 1 h and then at room temperature overnight. The light yellow crystals were collected by suction filtration and washed with H$_2$O (20 mL). The crystals were resuspended in H$_2$O (200 mL) and boiled briefly, followed by suction filtration, to collect the product which was dried under high vacuum. Yield: 35%.

Synthesis of compound P: Sodium t-butoxide (2 g, 20.8 mmoles) was added in one portion to a stirred solution of compound O (3 g, 18.9 mmoles) in 50 mL dry DMF. After all of the sodium t-butoxide was dissolved, iodomethane (1.3 mL) was added dropwise using a syringe. The stifling of the solution was continued at room temperature for 2 h and then the solution was poured into H$_2$O (150 mL). The product was extracted with EtOAc, and the extract was dried with anhydrous Na$_2$SO$_4$ and then evaporated to give crude compound P. The product was purified by separation on a silica gel column using 10% MeOH/CHCl$_3$ as the eluent. Yield: 70%.

Example 5

Synthesis of Transition Metal Complexes with Multiple Identical Ligands

Transition metal complexes containing multiple identical bidentate or tridentate ligands can be synthesized in one step from a metal halide salt and the ligand. This example illustrates the synthesis of an osmium complex with three identical 2,2'-biimidazole bidentate ligands.

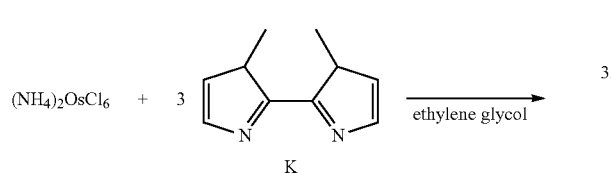

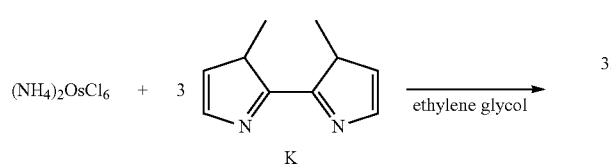

Synthesis of compound Q: Ammonium hexachloroosmate (200 mg, 0.46 mmoles) and compound K (221 mg, 1.37 mmoles) were mixed in 15 mL ethylene glycol in a 100 mL three-necked round bottom flask fitted with a reflux condenser. The mixture was degassed with N$_2$ for 15 min and then stirred under N$_2$ at 200-210° C. for 24 hrs. The solvent was removed by high vacuum distillation at 90-100° C. The green colored crude product was dissolved in 15 mL H$_2$O and stirred in air to be fully oxidized to the dark blue colored Os(III) oxidation state (about 24 h). The product was purified on a LH-20 reverse phase column using H$_2$O as the eluent. Yield: 50%.

Example 6

Synthesis of Transition Metal Complexes with Mixed Ligands

Transition metal complexes containing multiple types of ligands can be synthesized stepwise. First, a transition metal complex intermediate that contains one desired type of ligand and halide ligand(s), for example, chloride, is synthesized. Then the intermediate is subjected to a ligand substitution reaction to displace the halide ligand(s) with another desired type of ligand. The preparation of the following osmium complex illustrates the general synthetic scheme.

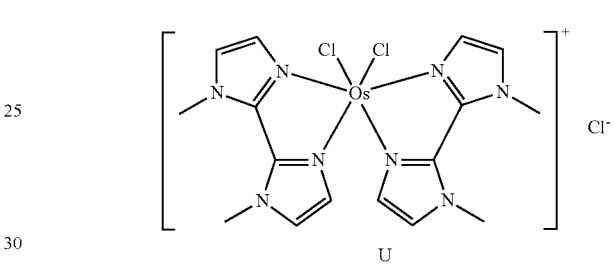

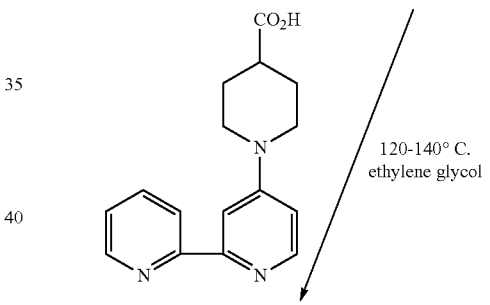

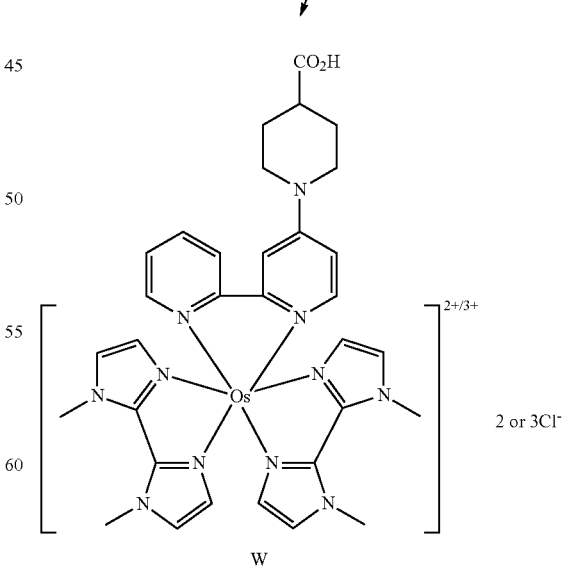

Synthesis of Compound U: Potassium hexachloroosmate (1 g, 2.08 mmoles), compound K (0.67 g, 4.16 mmoles) and LiCl (1 g, 23.8 mmoles) were suspended in 40 mL ethylene glycol in a 250 mL three-necked round bottom flask fitted with a reflux condenser. The suspension was degassed with $N_2$ for 15 min and then stirred under $N_2$ at 170° C. in an oil bath for 7-8 h, resulting in a dark brown solution. The solvent was removed by high vacuum distillation at 90-100° C. bath temperature. The gummy solid was triturated with acetone twice (2×50 mL) and then with $H_2O$ once (50 mL). The product was dried at 50° C. under high vacuum for 24 h.

Synthesis of compound W: A suspension of compound U (119 mg, 0.192 mmole) and 4-(4-carboxypiperidino)amino-2,2'-bipyridyl (prepared from compound E and ethyl isonipecotate using the synthetic methods for compounds F and G) was made in 10 mL ethylene glycol in a 100 mL three-necked round bottom flask equipped with a reflux condenser. The suspension was degassed with $N_2$ for 15 min and then stirred under $N_2$ at 130° C. in an oil bath for 24 h. The dark brown solution was cooled to room temperature and then poured into EtOAc (50 mL). The precipitate was collected by suction filtration. The dark brown solid thus obtained was compound W with osmium in a 2+ oxidation state. For ease of purification, the osmium 2+ complex was oxidized to an osmium 3+ complex by dissolving the dark brown solid in 20 mL $H_2O$ and stirring the solution in open air for 24 h. The resulting dark green solution was poured into a stirred solution of $NH_4PF_6$ (1 g) in 20 mL $H_2O$. The resulting dark green precipitate of $[Os(1,1'$-dimethyl-2,2'-biimidazole$)_2$(4-(4-carboxypiperidino)amino-2,2'-bipyridyl$)]^{3+}3PF_6^-$ was collected by suction filtration and washed with 5 mL $H_2O$ and then dried at 40° C. under high vacuum for 48 h. The counter anion $PF_6^-$ of $[Os(1,1'$-dimethyl-2,2'-biimidazole$)_2$(4-(4-carboxypiperidino)amino-2,2'-bipyridyl$)]^{3+}3PF_6^-$ was exchanged to the more water soluble chloride anion. A suspension of the $PF_6^-$ salt of compound W (150 mg) and $Cl^-$ resin (10 mL) in $H_2O$ (20 mL) was stirred for 24 h, at the end of which period all of osmium complex was dissolved. The dark green solution was separated by suction filtration and then lyophilized to give compound W.

Synthesis of [Os(4,4'-dimethoxy-2'2'-bipyridyl)$_2$(1-(3-aminopropyl)imidazole)]Cl$_3$

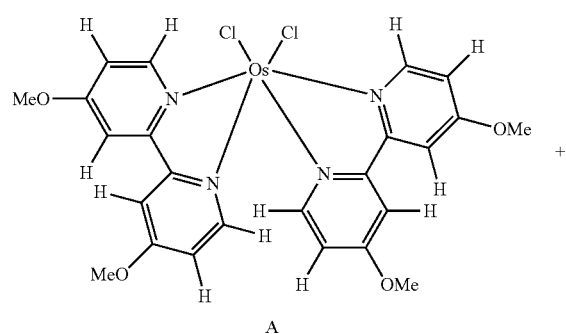

A suspension of compound A (prepared according to U.S. Pat. No. 5,393,903, incorporated herein by reference) (1.52 g) in 1 L anhydrous ethanol in a 3-necked round bottom flask fitted with a reflux condenser was degassed with $N_2$ for 15 min and then refluxed for 1 h. Compound B (259 µL) was added via a syringe over 10 min. and the resulting solution was refluxed for 24 h. The dark brown solution was cooled to room temperature and then concentrated to about 80 mL by rotary evaporation. Ethyl ether (about 400 mL) was added and the resulting mixture was degassed for 5 min. After standing at room temperature overnight, the resulting dark brown precipitate of compound C was collected by suction filtration. Yield: about 1 g.

Quaternization of Poly(4-vinylpyridine) with 6-Bromohexanoic Acid:

To compound D (2 g) dissolved in DMF was added 6-bromohexanoic acid (0.56 g). The resulting solution was stirred at 90° C. for 24 h. The solution was poured into 200 mL EtOAc under rapid stirring. The precipitate was collected by suction filtration, washed with EtOAc (2×20 mL) and then dried under high vacuum at 50 to 60° C. for 2 days. NMR (d$_6$-DMSO) indicated that about 15% of the pyridyl groups in the polymer were quaternized. Yield: 2.1 g.

Synthesis of Polymeric Osmium Complex G:
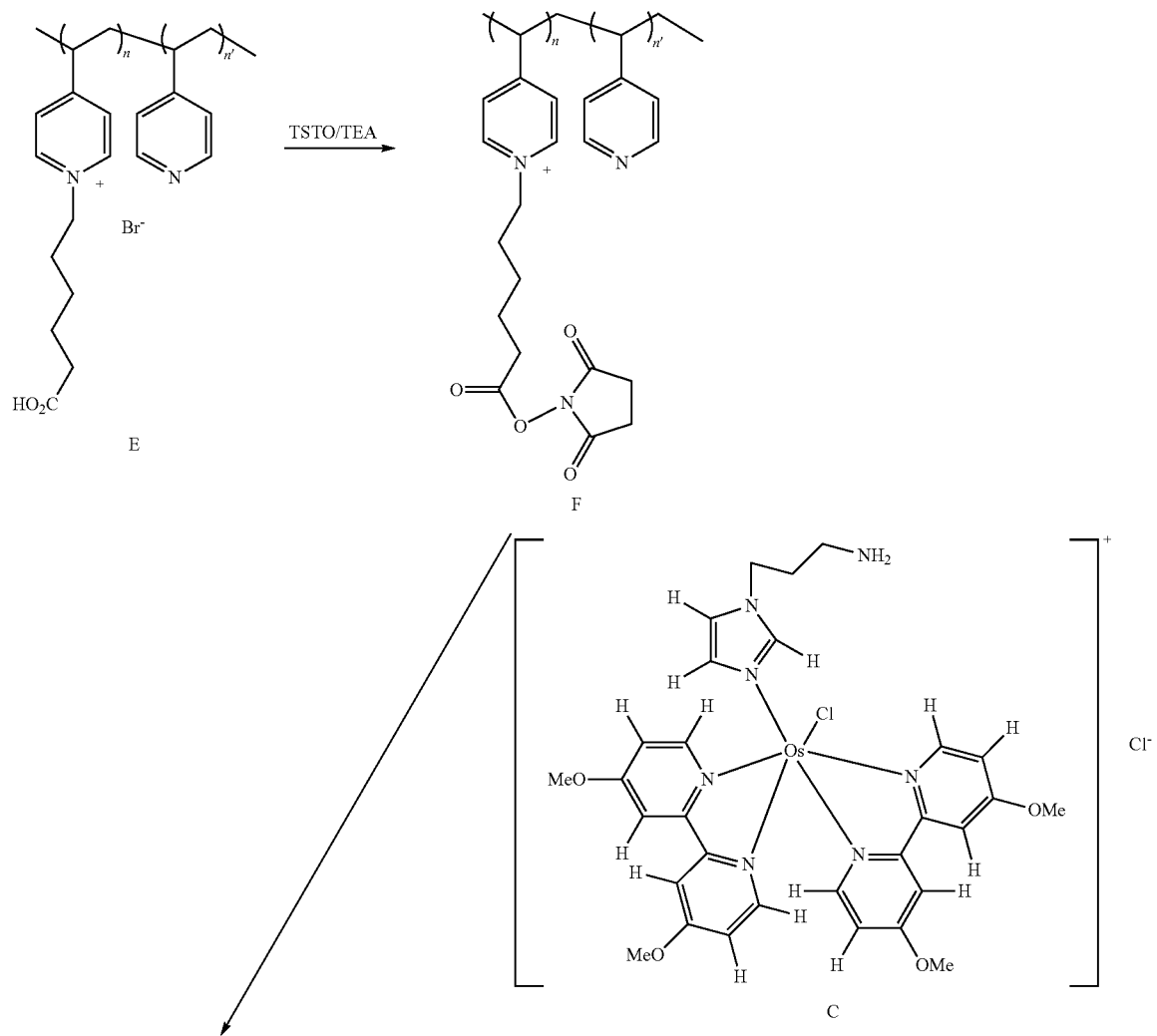
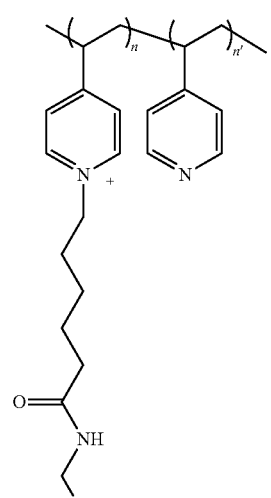

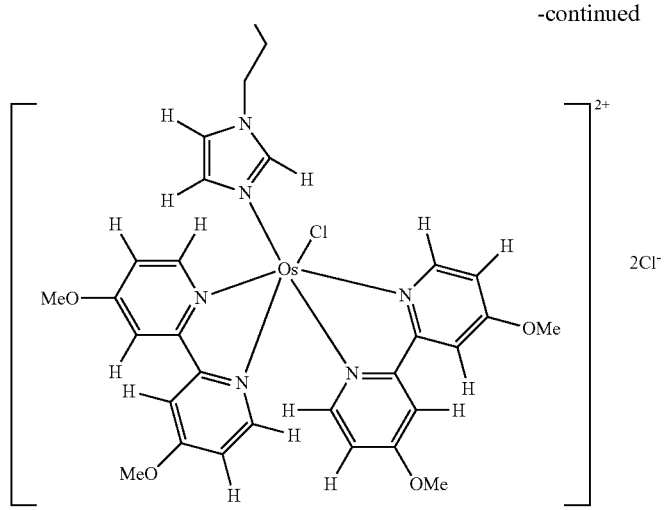

To a solution of compound E (71 mg) in 4 mL dry DMF was added O—(N-succinimidyl)-N,N,N',N'-tetramethyluronium tetrafluoroborate (TSTU) (24 mg). After the solution was stirred for 30 min, N,N,N-diisopropylethylamine (14 μL) was added and the resulting solution was stirred for 4 h. Compound C was added at once, followed by addition of another 14 μL N,N,N-diisopropylethylamine. The solution was continued to stir at room temperature for another 24 h. The dark brown solution was poured into 100 mL ether. The precipitate was collected by suction filtration, washed with ether (20 mL) and dried under vacuum at 50° C. for 24 h. The crude product was mixed with 30 mL chloride resin (AG 1×4, Bio-Rad Laboratories, Inc., Hercules, Calif.) in 50 mL H$_2$O and the resulting mixture was stirred in open air for 24 h. As the stirring continued, the insoluble polymeric Os(II) complex was slowly oxidized by air to the water soluble polymeric Os(III) complex with chloride as counter anions. The mixture was suction filtered and the filtrate was dialyzed by repeated ultrafiltration with H$_2$O (ultrafiltration membrane from Millipore, Corp., Bedford, Mass.: PM10, NMWL/10,000). The dialyzed polymer concentrate was diluted with H$_2$O to 10 mL and then freeze-dried to give compound G. Yield: 80 mg.

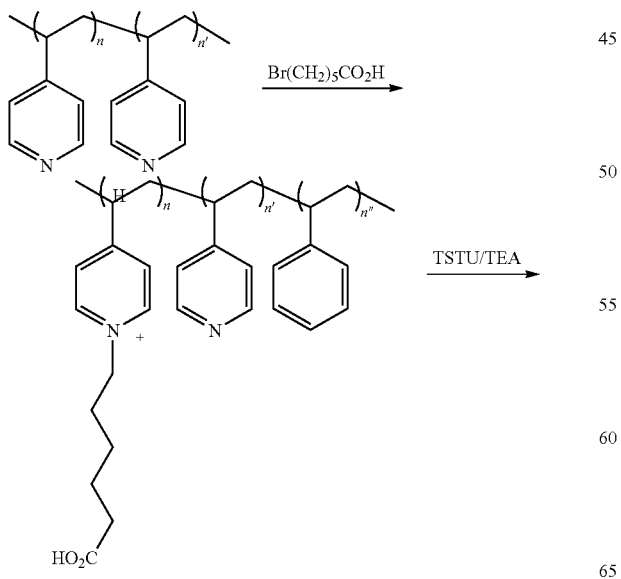

-continued

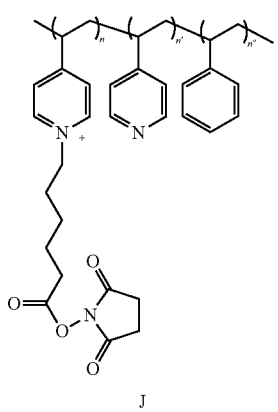

J

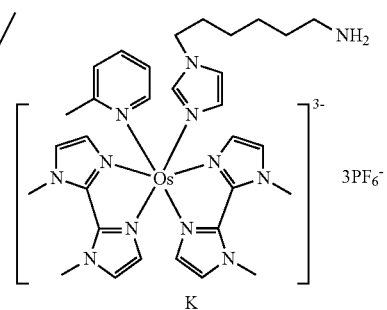

K

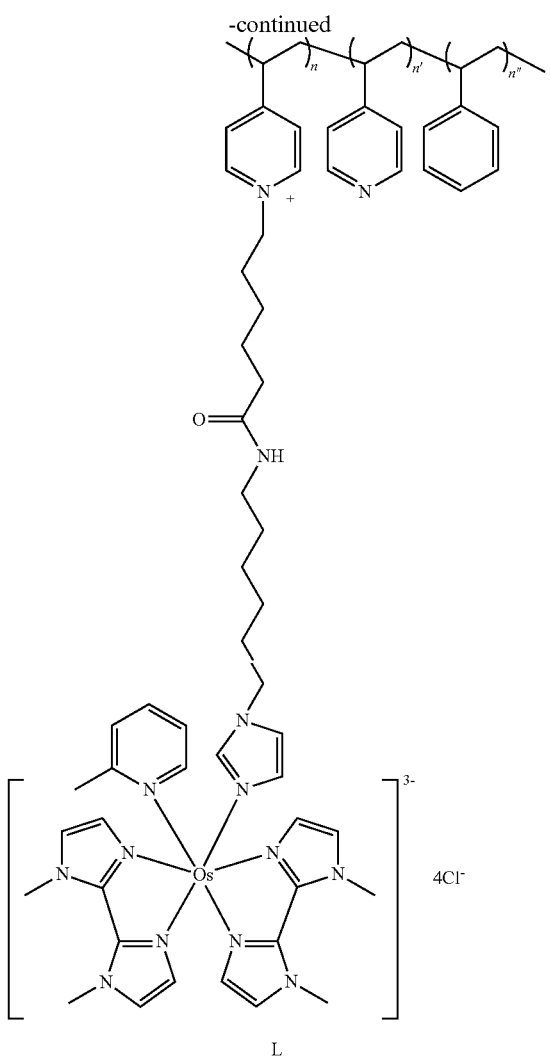

L

Synthesis of Compound I: Compound H (10% styrene, Aldrich) (2.37 g) was 5 dissolved in DMF (20 mL) by stifling the mixture at 90° C. for 3-4 h. 6-Bromohexanoic acid (0.66 g) was added portionwise over 10 min. and the resulting solution was stirred at 90° C. for 24 h. The solution was poured into 300 mL EtOAc and the precipitate was collected by suction filtration. The gummy product was redissolved in a minimum of methanol and precipitated out with ether (200 mL). The product was dried under high vacuum at 50° C. for 2 days.

Synthesis of 2-(6-Methyl-2-pyridyl)imidazole: A solution of 6-methylpyridine-2-carboxaldehyde (26 g, 0.21 mole) and glyoxal (40%, 30 mL) in 50 mL EtOH in a three-necked 250 mL round bottom flask fitted with a thermometer and an addition funnel was stirred in a NaCl/ice bath. When the solution was cooled to below 5° C., conc. $NH_4OH$ was added dropwise through the addition funnel. The rate of the addition was controlled so that the temperature of the solution was maintained at below 5° C. After the addition, the stifling of the yellow solution was continued in the ice bath for 1 h and then at room temperature overnight. The light yellow crystals were collected by suction filtration and washed with $H_2O$ (20 mL). The crystals were resuspended in $H_2O$ (200 mL) and boiled briefly, followed by suction filtration, to collect the product which was dried under high vacuum. Yield: 35%.

Synthesis of 2-(6-methyl-2-pyridyl)-1-(6-(phthalimido)hexyl)imidazole: To a solution of 2-(6-Methyl-2-pyridyl)imidazole (2.16 g) and sodium t-butoxide (1.57 g) in 50 mL dry DMF was added N-(6-bromohexyl)phthalimide (4.72 g). The resulting solution was stirred at room temperature for 3 h and then at 60° C. for 3.5 h. The solution was poured into $H_2O$ (80 mL) and then extracted three times with EtOAc (3×100 mL). The combined EtOAc extract was dried with anhydrous $Na_2SO_4$, and then evaporated to dryness. The product was purified by a silica gel column using EtOAc as the eluent. Yield: about 4.2 g.

Synthesis of 1-(6-Aminohexyl)-2-(6-methyl-2-pyridyl)imidazole: To a solution of 2-(6-methyl-2-pyridyl)-1-(6-(phthalimido)hexyl)imidazole (4.2 g) in 50 mL EtOH was added 1.5 mL hydrazine hydrate. The resulting solution was stirred at 80° C. overnight. The solution was cooled to room temperature and suction filtered to remove the precipitate. The filtrate was evaporated to give the crude product, which was purified by a silica gel column using 5% conc. $NH_3H_2O$/ $CH_3CN$ as the eluent. Yield: about 2.5 g.

Synthesis of 1,1'-Dimethyl-2,2'-biimidazole: To a stirred solution of 2,2'-biimidazole (Fieselmann, B. F., et al. *Inorg. Chem.* 17, 2078 (1978)) (4.6 g, 34.3 mmoles) in 100 mL dry DMF in a 250 ml round bottom flask cooled in an ice/water bath was added in portions NaH (60% in mineral oil, 2.7 g, 68.6 mmoles). After the solution was stirred at 0° C. for one hour under $N_2$, methyl toluenesulfonate (10.3 mL, 68.6 mmoles) was added in small portions using a syringe over 30 min. The stirring of the solution in the ice/water bath was continued for 1 h and then at room temperature for 3 h. The solvent was removed by vacuum distillation. The dark residue was triturated with ether and then suction filtered and dried under vacuum. The product was purified by sublimation. Yield: 80%.

Synthesis of [Os(1,1'-dimethyl-2,2'-biimidazole)$_2$Cl$_2$]Cl: Potassium hexachloroosmate (1 g, 2.08 mmoles), 1,1'-dimethyl-2,2'-biimidazole (0.67 g, 4.16 mmoles) and LiCl (1 g, 23.8 mmoles) were suspended in 40 mL ethylene glycol in a 250 mL three-necked round bottom flask fitted with a reflux condenser. The suspension was degassed with $N_2$ for 15 min and then stirred under $N_2$ at 170° C. in an oil bath for 7-8 h, resulting in a dark brown solution. The solvent was removed by high vacuum distillation at 90-100° C. bath temperature. The gummy solid was triturated with acetone twice (2×50 mL) and then with $H_2O$ once (50 mL). The product was dried at 50° C. under high vacuum for 24 h.

Synthesis of Compound K: A mixture of [Os(1,1'-dimethyl-2,2'-biimidazole)$_2$Cl$_2$]Cl (0.525 g) and 1-(6-aminohexyl)-2-(6-methyl-2-pyridyl)imidazole (0.248 g) is 40 mL ethylene glycol was degassed with $N_2$ for 10 min and then stirred under $N_2$ at 140° for 24 h. Ethylene glycol was removed by high vacuum distillation at 90° C. The residue was dissolved in 150 mL $H_2O$ and the resulting solution was stirred in open air for 24 h to allow full oxidation of Os(II) to Os(III). The solution was poured into a rapidly stirred solution of $NH_4PF_6$ (4.2 g) in 100 mL $H_2O$. The precipitate was collected by suction filtration and washed with $H_2O$ (2×10 mL). The 25 crude product was redissolved in 15 mL $CH_3CN$ and then added to a stirred solution of $NH_4PF_6$, (2.2 g) in 200 mL $H_2O$. The resulting precipitate was collected by suction filtration, washed with $H_2O$ (10 mL) and then dried under high vacuum at 45° C. Yield: about 0.6 g.

Synthesis of Compound L: the polymeric osmium complex was synthesized from polymer I and complex K using the method described above for compound G.

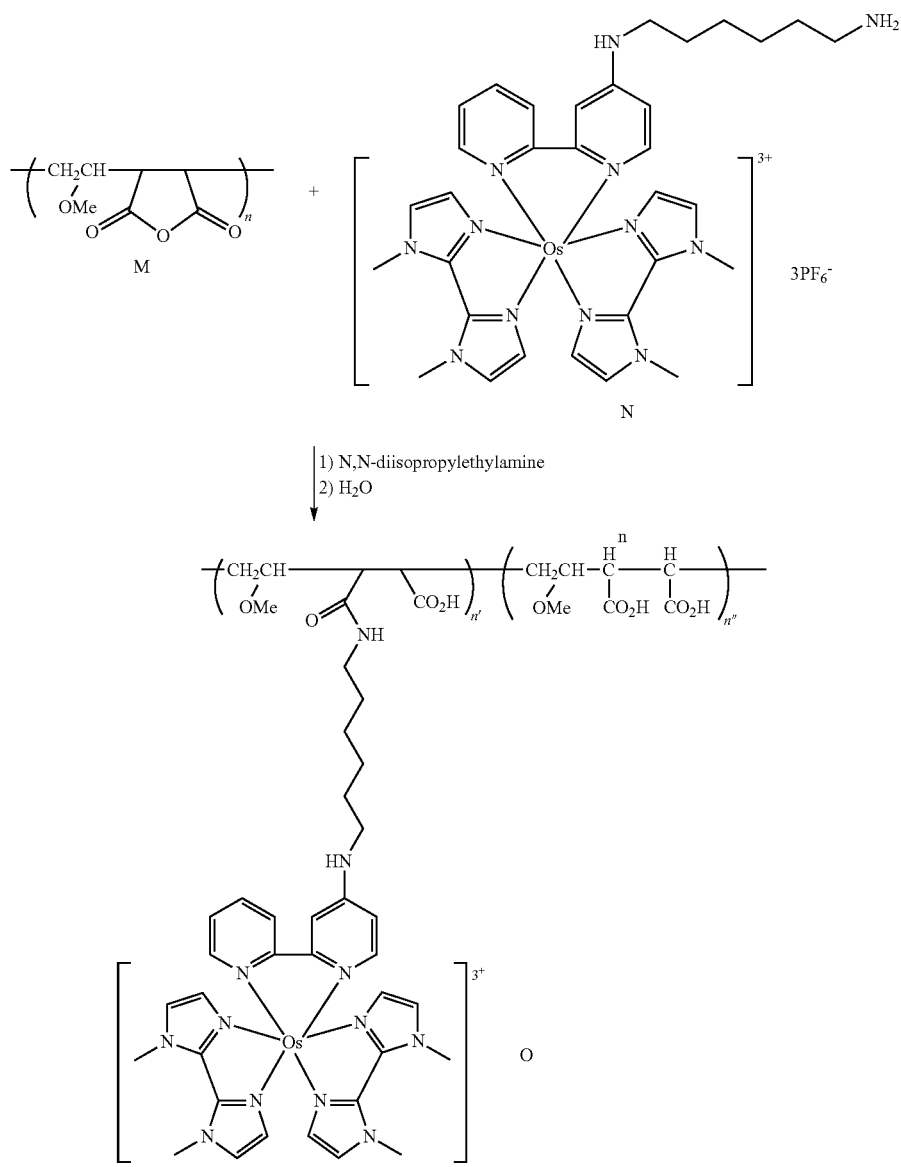

Synthesis of 4-bromo-2,2'-bipyridyl-N-oxide: To 4-nitro-2,2'-bipyridyl-N-oxide (Wenkert, D.; Woodward, R. B. *J. Org. chem.* 48, 283 (1983)) (5 g) dissolved in 30 mL acetic acid in a 100 ml round bottom flask was added 16 mL acetyl bromide. The yellow mixture was refluxed for 1.5 h and then rotovaporated to dryness. The resulting light yellow solid was sufficiently pure enough for the next step without further purification. Yield: 95%

Synthesis of 4-bromo-2,2'-bipyridyl: To a stirred suspension of 4-bromo-2,2'-bipyridyl-N-oxide in 60 mL $CHCl_3$, was added 12 mL $PCl_3$, at room temperature. The mixture was refluxed for 2 h under $N_2$ and then cooled to room temperature. The reaction mixture was poured into 100 mL ice/water. The aqueous layer was separated and saved. The $CHCl_3$, layer was extracted three times with $H_2O$ (3×60 mL) and then discarded. The combined aqueous solution was neutralized with $NaHCO_3$ powder to about pH 7-8. The resulting white precipitate was collected by suction filtration, washed with $H_2O$ (30 mL) and then dried under vacuum at 50° C. for 24 h. Yield: 85%.

Synthesis of a 4-((6-aminohexyl)amino)-2,2'-bipyridine: A mixture of 4-bromo-2,2'-bipyridyl (2.5 g) and 1,6-diaminohexane (15 g) in a 250 mL round bottom flask was heated under $N_2$ at 140° C. in an oil bath for 4-5 h. Excess 1,6-diaminohexane was removed by high vacuum distillation at 90-120° C. The product 20 was purified by a silica gel column, eluting with 5% $NH_4OH$ in isopropyl alcohol. Yield: 70%.

Synthesis of Compound N: Compound N was made from 4-((6-aminohexyl)amino)-2,2'-bipyridine and [Os(1,1'-dimethyl-2,2'-biimidazole)$_2$Cl$_2$]Cl using the method described for compound K.

Synthesis of Compound O: To a solution of compound M (37 mg, International Specialty Products, Wayne, N.J., USA) in 2 mL $CH_3CN$ and 0.5 mL THF was added compound N (51 mg), followed by the addition of two drops of N,N,N-diisopropylethylamine. The resulting solution was stirred at room temperature for 24 h. $H_2O$ (5 mL) was added and the solution was stirred for another 24 h. The solution was diluted with more $H_2O$ (50 mL) and dialyzed by repeated ultrafiltration as described above for the purification of compound G. The dialyzed solution was freeze-dried to give compound O.

The present invention should not be considered limited to the particular examples described above, but rather should be understood to cover all aspects of the invention as fairly set out in the attached claims. Various modifications, equivalent processes, as well as numerous structures to which the present invention may be applicable will be readily apparent to those of skill in the art to which the present invention is directed upon review of the instant specification.

That which is claims is:

1. A sensing layer comprising:
   a polymeric transition metal complex wherein the polymeric transition metal complex comprises:
      a transition metal complex comprising the formula:

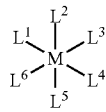

wherein M is a transition metal;
   $L^1$ is a ligand comprising a heterocycle and is coordinatively bound to M via a heteroatom of the heterocycle;
   $L^2$, $L^3$, $L^4$, $L^5$, and $L^6$ are ligands comprising a nitrogen-containing heterocycle, wherein each of $L^1$, $L^2$, $L^3$, $L^4$, $L^5$, and $L^6$ is independently a monodentate ligand or is combined with at least one other ligand to form a multidentate ligand; and
   wherein at least one of $L^1$, $L^2$, $L^3$, $L^4$, $L^5$, and $L^6$ is covalently coupled to the at least one spacer;
   an analyte-responsive enzyme;
   a polymer backbone; and
   at least one spacer covalently coupled to the polymer backbone, the at least one spacer comprising at least one non-cyclic functional group selected from the group consisting of —S(O)$_2$NR$^k$—, —OC(O)NR$^m$—, —OC(S)NR$^n$—, —C(O)NR$^t$—, —CR$^v$=N—O—, —CR$^w$=NNR$^x$—, and —(SiR$^y$R$^z$)—, and wherein R$^k$, R$^m$, R$^n$, R$^t$, R$^u$, R$^v$, R$^w$, R$^x$, R$^y$, and R$^z$ are independently hydrogen or substituted or unsubstituted alkyl,
      wherein the transition metal complex is covalently coupled to the spacer through the substituted or unsubstituted alkyl of the spacer.

2. The sensing layer of claim 1, wherein the analyte-responsive enzyme is an enzyme selected from the group consisting of glucose oxidase and glucose dehydrogenase.

3. The sensing layer of claim 1, wherein the analyte-responsive enzyme is covalently coupled to the polymer backbone.

4. The sensing layer of claim 1, wherein the polymer backbone comprises a nitrogen containing heterocyclic ring.

5. The sensing layer of claim 1, wherein the spacer comprises —C(O)NR$^t$—.

6. The sensing layer of claim 1, wherein the nitrogen-containing heterocycle comprises a substituted or unsubstituted pyridine, imidazole, 2,2'-bipyridine, 2-(2-pyridyl)imidazole, or 2,2'-biimidazole.

7. The sensing layer of claim 1, wherein at least two of $L^1$, $L^2$, $L^3$, $L^4$, $L^5$, and $L^6$ are combined to form at least one multidentate ligand.

8. The sensing layer of claim 1, wherein at least four of $L^1$, $L^2$, $L^3$, $L^4$, $L^5$, and $L^6$ are combined to form at least two multidentate ligand.

9. The sensing layer of claim 1, wherein at least four of $L^1$, $L^2$, $L^3$, $L^4$, $L^5$, and $L^6$ are combined to form at least two multidentate ligands selected from the group consisting of substituted and unsubstituted 2,2'-bipyridines, 2-(2-pyridyl)imidazoles, and 2,2'-biimidazoles.

10. The sensing layer of claim 7, wherein the transition metal complex comprises at least one substituted or unsubstituted 2,2'-biimidazole or 2-(2-pyridyl)imidazole.

11. The sensing layer of claim 1, wherein the polymer is crosslinked.

12. The sensing layer of claim 1, wherein the transition metal complex has the formula:

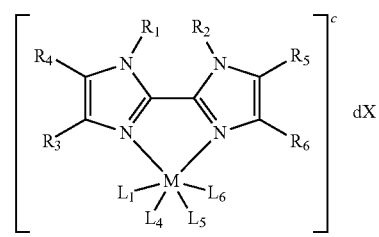

wherein M is a transition metal;
   $R_1$ and $R_2$ are independently substituted or unsubstituted alkyl;
   $R_3$, $R_4$, $R_5$, and $R_6$ are independently —H, —F, —Cl, —Br, or substituted or unsubstituted C1 to C12 alkyl;
      c is an integer selected from −1 to −5 or +1 to +5 indicating a positive or negative charge; X represents at least one counter ion; and
   d is an integer from 1 to 5 representing the number of counter ions, X.

13. The sensing layer of claim 1, wherein the transition metal complex has the formula:

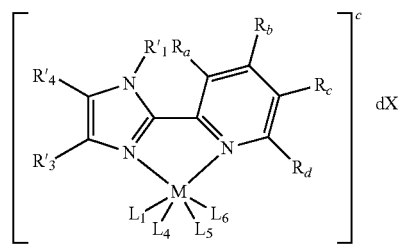

wherein M is a transition metal;
   $R'_1$ are substituted or unsubstituted alkyl;
   $R'_3$ and $R'_4$ and independently —H, —F, —Cl, —Br, or substituted or unsubstituted C1 to C12 alkyl;
   $R_a$, $R_b$, $R_c$ and $R_d$ are independently —H, —F, —Cl, —Br, —CN, —CO$_2$H, —SO$_3$H, —NO$_2$, —NH$_2$, —NHNH$_2$, —SH, or substituted or unsubstituted C1 to C12 alkylamino, C2 to C24 dialkylamino, C1 to C12 alkoxy, or C1 to C12 alkyl;
      c is an integer selected from −1 to −5 or +1 to +5 indicating a positive or negative charge; X represents at least one counter ion; and
   d is an integer from 1 to 5 representing the number of counter ions, X.

14. The sensing layer of claim 1, wherein the transition metal complex has the formula:

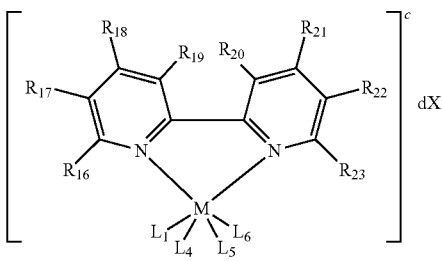

wherein M is a transition metal;

$R_{18}$ and $R_{21}$ are independently —H, —F, —Cl, —Br, —CN, —CO$_2$H, —SO$_3$H, —NO$_2$, —NH$_2$, —NHNH$_2$, —SH, or substituted or unsubstituted C1 to C12 alkylamino, C2 to C24 dialkylamino, C1 to C12 alkoxy, or C1 to C12 alkyl;

$R_{16}$, $R_{17}$, $R_{19}$, $R_{20}$, $R_{22}$ and $R_{23}$ —H or substituted or unsubstituted C1 to C12 alkyl;

c is an integer selected from −1 to −5 or +1 to +5 indicating a positive or negative charge; X represents at least one counter ion; and d is an integer from 1 to 5 representing the number of counter ions, X.

15. The sensing layer of claim 1, wherein the spacer comprises —S(O)$_2$NR$^k$—, wherein R$^k$, is hydrogen or substituted or unsubstituted alkyl.

16. The sensing layer of claim 1 wherein the spacer comprises —CR$^v$=N—O—, wherein R$^v$, is hydrogen or substituted or unsubstituted alkyl.

17. The sensing layer of claim 1, wherein the spacer comprises —CR$^w$=NNR$^x$—, wherein R$^w$ and R$^x$ are independently hydrogen or substituted or unsubstituted alkyl.

18. The sensing layer of claim 1, wherein the spacer comprises —(SiR$^y$R$^z$)—, wherein R$^y$ and R$^z$ are independently hydrogen or substituted or unsubstituted alkyl.

* * * * *